United States Patent
Spence

(10) Patent No.: US 10,627,415 B2
(45) Date of Patent: Apr. 21, 2020

(54) COMPOSITIONS AND METHODS FOR DIAGNOSING, MONITORING, AND TREATING AN AUTOIMMUNE DISEASE

(71) Applicant: BOARD OF TRUSTEES OF MICHIGAN STATE UNIVERSITY, East Lansing, MI (US)

(72) Inventor: Dana Spence, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

(21) Appl. No.: 15/557,765

(22) PCT Filed: Mar. 11, 2016

(86) PCT No.: PCT/US2016/022148
§ 371 (c)(1),
(2) Date: Sep. 12, 2017

(87) PCT Pub. No.: WO2016/145389
PCT Pub. Date: Sep. 15, 2016

(65) Prior Publication Data
US 2018/0095097 A1    Apr. 5, 2018

Related U.S. Application Data

(60) Provisional application No. 62/132,213, filed on Mar. 12, 2015.

(51) Int. Cl.
| | | |
|---|---|---|
| *G01N 33/74* | (2006.01) | |
| *G01N 33/80* | (2006.01) | |
| *G01N 33/50* | (2006.01) | |
| *A61K 38/21* | (2006.01) | |

(52) U.S. Cl.
CPC ......... *G01N 33/74* (2013.01); *G01N 33/5005* (2013.01); *G01N 33/80* (2013.01); *A61K 38/215* (2013.01); *G01N 2333/62* (2013.01); *G01N 2333/765* (2013.01); *G01N 2800/24* (2013.01); *G01N 2800/285* (2013.01)

(58) Field of Classification Search
None
See application file for complete search history.

(56) References Cited

U.S. PATENT DOCUMENTS

| | | | |
|---|---|---|---|
| 3,710,795 A | 1/1973 | Higuchi et al. | |
| 4,863,457 A | 9/1989 | Lee | |
| 5,491,216 A | 2/1996 | Hoffmann et al. | |
| 5,501,856 A | 3/1996 | Ohtori et al. | |
| 6,001,329 A | 12/1999 | Buchsbaum et al. | |
| 6,558,924 B1 | 5/2003 | Stahl et al. | |
| 8,691,755 B2 | 4/2014 | Barrack et al. | |
| 2002/0160435 A1 | 10/2002 | Kitajima et al. | |
| 2005/0037448 A1 | 2/2005 | Bouanani et al. | |
| 2008/0241223 A1 | 10/2008 | Nivaggioli et al. | |
| 2009/0171070 A1 | 7/2009 | Van Urk et al. | |
| 2011/0020471 A1 | 1/2011 | Spence et al. | |
| 2012/0165509 A1 | 6/2012 | Yang et al. | |
| 2014/0141509 A1 | 5/2014 | Gadue et al. | |

FOREIGN PATENT DOCUMENTS

| | | |
|---|---|---|
| CN | 103852584 A | 6/2014 |
| EP | 0319067 A1 | 6/1989 |
| EP | 430539 A2 | 6/1991 |
| EP | 488401 A1 | 6/1992 |
| EP | 1191337 A2 | 3/2002 |
| WO | WO-2006055871 A2 | 5/2006 |
| WO | WO-2014094406 A1 | 6/2014 |

OTHER PUBLICATIONS

Meyer et al., Zinc-activated C-peptide resistance to the type 2 diabetic erythrocyte is associated with hyperglycemia-induced phosphatidylserine externalization and reversed by metformin, (2009), Mol. BioSyst. 5:1157-1162.*

Lockwood et al., An In Vitro Diagnostic for Multiple Sclerosis Based on C-peptide Binding to Erythrocytes, (2016), EBioMedicine 11: 249-252.*

Hills et al., Intracellular Signalling by C-Peptide, (2008), Experimental Diabetes Research vol. 2008, Article ID 635158, 8 pages, doi:10.1155/2008/635158.*

Liu et al., C-peptide and zinc delivery to erythrocytes requires the presence of albumin: implications in diabetes explored with a 3D-printed fluidic device, (Jul. 2015), Integr. Biol. 7:534-543.*

Rigler et al., "Specific binding of proinsulin C-peptide to human cell membranes", Proc Natl Acad Sci USA, Nov. 9, 1999 (Sep. 11, 1999), vol. 96, pp. 13318-13323.

Flatt et al., "Specific Binding of the C-Peptide of Proinsulin to Cultured B-Cells from a Transplantable Rat Islet Cell Tumor", Biosdience Reports, Feb. 1, 1986 (Feb. 1, 1986), vol. 6, pp. 193-199.

Klein et al., "Albumin-bound basal insulin analogues (insulin detemir and NN344): comparable time-action profiles but less variability than insulin glargine in type 2 diabetes", Diabetes Obes Metab., May 1, 2007 (May 1, 2007), vol. 9, pp. 290-299.

Kunt et al., "The effect of human proinsulin C-peptide on erythrocyte deformability in patients with Type 1 diabetes mellitus", Diabetologia, Apr. 1, 1999 (Apr. 1, 1999), vol. 42, pp. 465-471.

(Continued)

*Primary Examiner* — John D Ulm
(74) *Attorney, Agent, or Firm* — Harness, Dickey & Pierce, PLC

(57) ABSTRACT

Compositions and methods for measuring C-peptide binding by cells, including cells expressing Glut1, using a C-peptide binding facilitator, such as an albumin. Such methods include incubating the cell with a known amount of C-peptide and a C-peptide binding facilitator, and determining the amount of C-peptide bound to the incubated cells. Also provided are methods for detecting, monitoring, and/or treating immune-mediated diseases, such as multiple sclerosis (MS), using method of the present technology for measuring C-peptide binding by cells obtained from a human or other animal subject.

15 Claims, 9 Drawing Sheets

Specification includes a Sequence Listing.

(56) References Cited

OTHER PUBLICATIONS

Doughty et al., "Antigen receptor-mediated changes in glucose metabolism in B lymphocytes: role of phosphatidylinositol 3-kinase signaling in the glycolytic control of growth", Blood, Jun. 1, 2006 (Jan. 6, 2006), vol. 107, pp. 4458-4465.

Meyer et al., "Metal-activated C-peptide Facilitates Glucose Clearance and the Release of a Nitric Oxide Stimulus via the GLUT1 Transporter", Diabetologia, Oct. 27, 2007 (Oct. 27, 2009), vol. 51, pp. 175-182.

International Search Report and Written Opinion of the International Searching Authority issued in PCT/US2016/022148, dated Jun. 21, 2016; ISA/US.

Dockal, Michael et al., "Five recombinant fragments of human serum albumin—Tools for the characterization of the warfarin binding site." Protein Science, vol. 9, 2000, pp. 1455-1465.

Faris, Andrea and Spence, Dana M., "Measuring the simultaneous effects of hypoxia and deformation on ATP release from erythrocytes." Analyst, vol. 133, No. 5, 2008, pp. 678-682.

Fischer, David J. et al., "Determination of erythrocyte deformability and its correlation to cellular ATP release using microbore tubing with diameters that approximate resistance vessels in vivo." Analyst, vol. 128, No. 9, 2003, pp. 1163-1168.

Hanauske, Axel-R. et al., "Phase 1 b Dose Escalation Study of Erlotinib in Combination with Infusional 5-Fluorouracil, Leucovorin, and Oxaliplatin in Patients with Advanced Solid Tumors." Clinical Cancer Research, vol. 13, No. 2, 2007, pp. 523-531.

Hetherington, Seth et al., "Phase I Dose Escalation Study to Evaluate the Safety and Pharmacokinetic Profile of Tefibazumab in Subjects with End-Stage Renal Disease Requiring Hemodialysis." Antimicrobial Agents and Chemotherapy, vol. 50, No. 10, Oct. 2006, pp. 3499-3500.

Horn, N. M. et al., "The effect of histidine and cysteine on zinc influx into rat and human erythrocytes." Journal of Physiology, vol. 489, No. 1, 1995, pp. 73-80.

Knight, Linda C., "Radiolabeled Peptides for Tumor Imaging." Handbook of Radiopharmaceuticals: Radiochemistry and Applications, John Wiley & Sons, 2003, ISBN: 0471495603, pp. 643-682.

McDonald, W. I. et al. "Are magnetic resonance findings predictive of clinical outcome in therapeutic trials in multiple sclerosis? The dilemma of interferon-beta." Annals of Neurology, vol. 36, No. 1, Jul. 1994, pp. 14-18.

Medawala, Wathsala et al., "A Molecular Level Understanding of Zinc Activation of C-peptide and its Effects on Cellular Communication in the Bloodstream." The Review of Diabetic Studies, vol. 6, No. 3, 2009, pp. 148-158.

Nordquist, Lina et al., "Renal and vascular benefits of C-peptide: Molecular mechanisms of C-peptide action." Biologics: Targets and Therapy, vol. 2, No. 3, 2008, pp. 441-452.

Paty, D. W. et al., "Interferon beta-1b is effective in relapsing-remitting multiple sclerosis." Neurology, vol. 43, No. 4, 1993, pp. 662-667.

Petruzzi, Enrico et al. "Adenosine triphosphate release by osmotic shock and hemoglobin $A_{1c}$ in diabetic subjects' erythrocytes." Metabolism, vol. 43, No. 4, Apr. 1994, pp. 435-440.

Richards, Jennifer P. et al. "Low $O_2$-induced ATP release from erythrocytes of humans with type 2 diabetes is restored by physiological ratios of C-peptide and insulin." American Journal of Physiology—Regulatory, Integrative and Comparative Physiology, vol. 307, No. 7, 2014, pp. R862-R868.

Richards, Jennifer P. et al., "Synergistic effects of C-peptide and insulin on low $O_2$-induced ATP release from human erythrocytes." American Journal of Physiology—Regulatory, Integrative and Comparative Physiology, vol. 305, No. 11, 2013, pp. R1331-R1336.

Rogers, Buck E. et al., "Localization of Iodine-125-mIP-Des-Met[14]-Bombesin (7-13)$NH_2$ in Ovarian Carcinoma Induced to Express the Gastrin Releasing Peptide Receptor by Adenoviral Vector-Mediated Gene Transfer." The Journal of Nuclear Medicine, vol. 38, No. 8, Aug. 1997, pp. 1221-1229.

Van Gurp, E. et al., "Phase 1 Dose-Escalation Study of CP-690 550 in Stable Renal Allograft Recipients: Preliminary Findings of Safety, Tolerability, Effects on Lymphocyte Subsets and Pharmacokinetics." American Journal of Transplantation, vol. 8, 2008, pp. 1711-1718.

\* cited by examiner

COMPOSITIONS AND METHODS FOR DIAGNOSING, MONITORING, AND TREATING AN AUTOIMMUNE DISEASE

CROSS-REFERENCE TO RELATED APPLICATIONS

This application is a National Phase of International Patent Application PCT/US2016/022148, filed Mar. 11, 2016, which claims the benefit of U.S. Provisional Application No. 62/132,213, filed on Mar. 12, 2015. The entire disclosure of the above applications is are incorporated herein by reference.

BACKGROUND

The present technology relates to compositions and in vitro methods for measuring C-peptide binding by cells. Such compositions and methods may be used in methods of diagnosing, monitoring, and treating multiple sclerosis (MS) and other immune-mediated or autoimmune diseases.

MS is a demyelinating disease that is associated with the immune-mediated destruction of myelin that insulates and protects axons in the central nervous system. MS is one of a group of disorders that can be characterized as autoimmune diseases.

About 1 in 1,000 people in the United States has MS, while about 1-2 million people worldwide are thought to have MS. The number of people tested for MS is significantly higher. This is largely because not all symptoms are present in all MS patients, and MS can be characterized, in some cases, as episodic, with short to long periods of clinical remission. Common symptoms of MS include, e.g., fatigue, weakness, spasticity, balance problems, bladder and bowel problems, numbness, vision loss, tremor and vertigo. Due to the broad range of symptoms and the manner in which they present (which may be very subtle), the diagnosis of MS may take months to years. For example, physicians often must combine detailed patient histories and perform both neurological and physiological examinations of people presenting with symptoms. A definitive diagnosis of MS requires time (i.e., at least two separate symptomatic events or changes on Magnetic Resonance Imaging, MRI, over time) and measurable dissemination of the disease (i.e., at least two separate locations within the central nervous system, which can be demonstrated by MRI or neurological exam). Thus, proper and effective treatment of patients may be delayed during this diagnostic phase. Furthermore, current tests for MS can be costly and invasive—e.g., MRI scans, electrophysiological tests, and analysis of cerebrospinal fluid. In short, there is a need for new methods and compositions for diagnosing MS and other immune-mediated diseases.

SUMMARY

The present technology is based, at least in part, on the discovery that albumin facilitates the uptake of C-peptide and $Zn^{2+}$, $Fe^{2+}$, and/or $Cr^{3+}$ by red blood cells (RBCs), i.e., erythrocytes, in vitro. In various embodiments, the present technology exemplifies the use of a C-peptide binding facilitator, such as an albumin, in methods for detecting or otherwise measuring C-peptide binding by RBCs. As discussed below, without limiting the scope or function of the present technology, it has been found that RBCs from patients with MS exhibit increased C-peptide uptake and $Zn^{2+}$, $Fe^{2+}$, and/or $Cr^{3+}$ uptake, with concomitant adenosine triphosphate (ATP) release, relative to RBCs from healthy humans without MS. In some embodiments, the present technology provides a variety of diagnostic and therapeutic applications (e.g., methods for diagnosing and/or treating an immune-mediated/autoimmune disease, such as MS), which involve the methods of measuring C-peptide binding to cells, or information derived therefrom.

Accordingly, in one aspect, the present technology provides in vitro methods for measuring C-peptide binding to cells, such as RBCs or other cells expressing the glucose 1 transporter protein (Glut1). Such methods comprise incubating the cells with a C-peptide mixture comprising an amount, which may be a known amount, of C-peptide and a C-peptide binding facilitator to produce incubated cells in an incubated cellular mixture, and determining the amount of C-peptide that bound to the incubated cells.

In some embodiments, C-peptide binding facilitators comprise albumins, leptin, collagen, and mixtures thereof. In various preferred embodiments, the C-peptide binding facilitator is an albumin, is human albumin or a non-human albumin (e.g., bovine). In some embodiments, the albumin is obtained from plasma, serum, or whole blood of a mammal. In some embodiments, the albumin is recombinantly produced albumin. In some embodiments, the albumin is a variant form of a naturally-occurring albumin protein, e.g., one that shares at least 80 (e.g., at least 85, 90, 95, or 99) % identity with a naturally-occurring albumin protein (e.g., human albumin).

In various embodiments, the C-peptide may be a polypeptide comprising the amino acid sequence EGSLQ (SEQ ID NO:17). For example, the C-peptide is selected from the group consisting of a full length wild type C-peptide, a C-peptide molecule having an amino acid sequence at least 75% identical to the amino acid sequence of wild type C-peptide, fractions thereof comprising at least 5 amino acids, and combinations thereof, wherein the C-peptide has the ability to bind to cells in the presence of the C-peptide binding facilitator.

For example, such methods may comprise contacting, in the presence of albumin, a RBC (or a plurality of RBCs) with C-peptide to form a mixture; incubating the mixture under conditions that allow for binding of C-peptide by the RBC or cells; and determining the binding (e.g., determining the uptake) of C-peptide by the RBCs. The binding can be determined by measuring the amount of C-peptide not bound by the cell or cells; the amount of C-peptide bound by the cell or cells; the amount of C-peptide not bound by the cell or cells; and/or the resultant ATP release from the cells contacted with C-peptide (e.g., C-peptide and $Zn^{2+}$).

In some embodiments of any of the methods described herein, the amount of C-peptide present in the RBCs after the incubation is measured as the measure of binding or uptake. In some embodiments, the amount of free C-peptide in the mixture remaining after the incubation is measured as the measure of binding or uptake. In some embodiments, binding or uptake of C-peptide by the RBCs is measured as a function of the amount of ATP released from the RBCs after the incubation.

Thus, in various embodiments, determining the binding of C-peptide may be assessed by direct measurement of binding of C-peptide by cells, or indirectly such as through measuring the amount of C-peptide that is not bound by the cells. For example, the determining of an amount of C-peptide bound to the incubated cells may comprise:

separating the incubated cells from the incubated cellular mixture, forming an incubated cell fraction and a supernatant; and measuring (i) the amount of C-peptide in the incubated cellular fraction; or
(ii) the amount of C-peptide in the supernatant; or
(iii) a combination of (i) and (ii).

In some embodiments, the amount of C-peptide bound by cells is determined by incubating cells with a known amount of C-peptide, separating the incubated cells to form a supernatant, and measuring the amount of C-peptide in the supernatant. The amount is then determined by subtracting the amount of C-peptide in the supernatant from the known amount of C-peptide.

Measuring C-peptide may be performed by methods among those known in the art. For example, the measuring may comprise directly detecting C-peptide by detecting a signal provided by a tag coupled to the C-peptide or indirectly detecting C-peptide by detecting an antibody or antibody fraction that binds to the C-peptide.

The present technology also provides in vitro methods for assessing the status of an immune-mediated disease in a mammalian subject, for example assessing the probability that a mammalian subject has an immune-mediated disease, the method comprising:

incubating cells that express Glut1 obtained from the subject with a C-peptide composition comprising an amount, e.g., a known amount, of C-peptide and an albumin under conditions that allow for the cells to bind the C-peptide to form incubated cells in an incubated cellular mixture;

separating the incubated cells from the incubated cellular mixture; and determining the amount of C-peptide bound to the incubated cells.

In yet another aspect, the present technology features an in vitro method for assessing the probability that a mammalian subject has an immune-mediated disease. The method includes: contacting cells that express Glut1 obtained from the subject with an amount, e.g., a known amount, of C-peptide and an albumin to form a C-peptide cellular mixture; incubating the C-peptide cellular mixture under conditions that allow for the cells to bind the C-peptide, to form incubated cells in an incubated cellular mixture; separating the incubated cells from the incubated cellular mixture; and determining the amount of C-peptide bound to the incubated cells.

The present technology also provides in vitro methods for diagnosing a mammalian subject as having an immune-mediated disease, such methods comprising:

incubating, in the presence of albumin, RBCs from the subject with C-peptide under conditions that allow for binding of C-peptide by RBCs; and determining the amount of C-peptide bound by the RBCs, wherein increased binding of C-peptide by the RBCs, relative to a control C-peptide binding level, indicates that the subject has the immune-mediated disease. Associated methods include those for managing MS in a subject in need thereof, the method comprising:

(a) effecting an assay for measuring C-peptide binding on cells obtained from the subject, the assay comprising
  (i) incubating the cells with a C-peptide composition comprising an amount, e.g., a known amount, of C-peptide and a C-peptide binding facilitator to produce incubated cells in an incubated cellular mixture; and
  (ii) determining the amount of C-peptide bound to the incubated cells.

(b) comparing the amount of C-peptide bound by the cells to a reference amount determined by performing the assay on cells obtained from a second subject that does not have the immune-mediated disease;
(c) administering a first treatment for MS; and
(d) assessing the efficacy of the administering by repeating the effecting and comparing.

The present technology also provides kits for use measuring C-peptide binding by cells, the kit comprising a C-peptide binding facilitator, C-peptide, and a container. The container may be operable for mixing a solvent with one or both of the C-peptide binding facilitator and the C-peptide. In various embodiments, the container is a first container containing the C-peptide binding facilitator, and the kit further comprises a second container containing C-peptide. The C-peptide binding facilitator may be albumin in powdered form, preferably wherein the albumin is lyophilized. In various embodiments, the kit further comprises a third container containing a solvent for one or both of the C-peptide binding facilitator and the C-peptide. For example, the solvent may comprise phosphate buffered saline, physiological saline solution, tris(hydroxymethyl)aminomethane (Tris) buffer, or phosphate buffer.

The present technology also provides reagents for use in measuring C-peptide binding to cells that express Glut1, the reagent consisting essentially of albumin dissolved in an isotonic solution and, optionally, further consisting of an optional component selected from the group consisting of C-peptide, a buffering agent, $Zn^{2+}$, $Fe^{2+}$, $Cr^{3+}$, and mixtures thereof. Also provided are reagents for use in measuring C-peptide binding to cells that express Glut1, the reagent consisting essentially of C-peptide dissolved in an isotonic solution and, optionally, further consisting of an optional component selected from the group consisting of albumin, a buffering agent, $Zn^{2+}$, $Fe^{2+}$, $Cr^{3+}$, and mixtures thereof. For example, the buffering agent may be selected from the group consisting of phosphate salts, Tris, and mixtures thereof.

DRAWINGS

The drawings described herein are for illustrative purposes only of selected embodiments and not all possible implementations, and are not intended to limit the scope of the present technology.

FIG. 1 is a bar graph depicting the level of C-peptide uptake by RBCs from patients with multiple sclerosis (MS) (n=25) and healthy human volunteers (control or C) (n=17). The Y axis represents C-peptide binding in picomoles.

FIG. 2 is a diagram of an exemplary kit composition. The kit includes 3 vials and an ELISA well. In (A) buffer is moved from the first vial to a second vial that contains solid albumin. In (B), the content of the third vial, C-peptide in water, is moved to the vial now containing the albumin in buffer. In (C) red blood cells (RBCs) from the donor are added to the vial containing C-peptide and albumin in buffer. This solution is centrifuged and analyzed by ELISA for remaining C-peptide in the supernatant. This value is subtracted from the moles of C-peptide originally in the vial #3 (typically 20 picomoles), resulting in the amount of C-peptide bound to the RBCs.

FIG. 3 is a bar graph depicting the results from the adenosine triphosphate (ATP) release studies, showing that the ATP release from the RBCs of MS patients was found to be an average of 344.7±46.8 nM where the average release from healthy controls was 132.1±14.1 nM. When the RBCs of the MS patients were incubated with a CFTR inhibitor, glybenclamide, the ATP release is decreased below the amount of the healthy controls, to a level of 65.3±11.6 nM, suggesting that the increase in ATP release of the flowing RBCs of MS patients is not the result of RBC lysis. The error is reported as standard error of the mean, for N=19 MS patients, 10 healthy controls and 12 glybenclamide inhibitions.

FIG. 4 is a bar graph depicting that the amount of $^{65}Zn^{2+}$ able to bind with the RBCs of MS patients is significantly higher, at a value of 3.61±0.22 picomoles, than that of healthy controls, at a value of 2.26±0.24 picomoles. The amount of C-peptide binding to the RBC correlates to this very well, as shown in FIG. 1. The error is reported as standard error of the mean for N=22 MS patients and 11 healthy controls.

Corresponding reference numerals indicate corresponding parts throughout the several views of the drawings.

DETAILED DESCRIPTION

Figure 1:
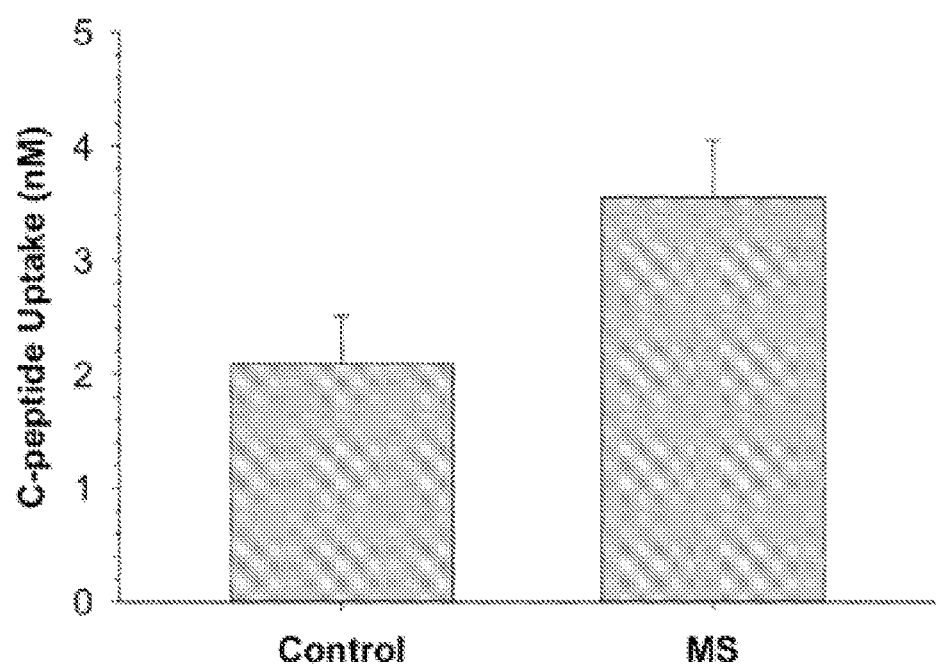

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. In particular, the following description sets forth example embodiments and otherwise provides information that enables a person skilled in the art to make and use the subject matter set forth in the appended embodiments, but may omit certain details already well-known in the art. The following description is, therefore, to be taken as illustrative and not limiting. A non-limiting discussion of terms and phrases intended to aid understanding of the present technology is provided at the end of this Detailed Description.

The present technology provides, among other things, methods, compositions, reagents and kits that are useful for in vitro methods for measuring the binding of C-peptide to cells. Also provided are associated diagnostic methods, as well as therapeutic applications, which are useful for detecting, monitoring, and/or treating immune-mediated diseases, which affect such in vitro methods or involve use of information obtained from such in vitro methods.

In general, the present technology includes in vitro methods (also referred to herein as "assays") comprising:
incubating cells with C-peptide mixture comprising a known or unknown amount of C-peptide and a C-peptide binding facilitator to produce incubated cells in an incubated cellular mixture; and
determining the amount of C-peptide bound to the incubated cells.

Determining the amount of C-peptide bound to the incubated cells generally includes separating the incubated cells from the incubated cellular mixture, forming an incubated cell fraction and a supernatant; and measuring:
(i) the amount of C-peptide in the incubated cellular fraction; or
(ii) the amount of C-peptide in the supernatant; or
(iii) the amount of C-peptide in the supernatant, and subtracting the amount of C-peptide in the supernatant from a known amount of C-peptide; or
(iv) any combination of (i), (ii), and (iii).

Embodiments described herein can involve, e.g., contacting, in the presence of a C-peptide binding facilitator, such as albumin, RBCs from a subject of interest with C-peptide to form a mixture.

Materials

C-Peptide

C-peptide, also known as the connecting peptide, is an approximately 30 amino acid polypeptide that connects the A and B chain of mature insulin within the proinsulin molecule. Proteolytic processing of proinsulin to mature insulin liberates the C-peptide. In addition to facilitating the proper folding of insulin, C-peptide possesses characteristics of a hormone, stimulating intracellular signaling mechanisms and even inducing beneficial physiological effects in renal and vascular tissues from diabetic subjects. Nordquist et al. (2008) *Biologics* @:441-452. C-peptide has been shown to facilitate $Zn^{2+}$, $Fe^{2+}$, and/or $Cr^{3+}$ delivery to RBCs, and to stimulate the release of ATP from RBCs in a $Zn^{2+}$-, $Fe^{2+}$-, and/or $Cr^{3+}$-dependent manner. Medawala et al. (2009) *Rev Diabetic Studies* @:148. The cellular effects of this $Zn^{2+}$, $Fe^{2+}$, and/or $Cr^{3+}$ delivery are manifold; glucose uptake is significantly enhanced into the cells, and ATP release from the cells is also increased. That latter feature is important for maintenance of proper blood flow, as ATP is a known stimulus of nitric oxide (NO) production in endothelial cells and is also an established vessel dilator and platelet inhibitor.

The term "C-peptide" as used herein includes all forms of C-peptide (also known as proinsulin C-peptide), including naturally derived, native, synthetic peptides or semi-synthetic peptides. Such C-peptides may be may be isolated from any species, including the human peptide, peptides from other animal species and genera, preferably mammals. In various embodiments, the C-peptide comprises carboxyl C-peptide pentapeptide having the sequence EGSLQ (SEQ ID NO:17) In various embodiments, the C-peptide is a fraction of a corresponding full length C-peptide having at least 5 amino acids.

As referred to herein, the terms "polypeptide," "peptide," and "protein" are used interchangeably and mean any peptide-linked chain of amino acids, regardless of length or post-translational modification. As noted below, the polypeptides described herein can be, e.g., wild-type proteins, functional fragments of the wild-type proteins, or variants of the wild-type proteins or fragments. Variants, in accordance with the present technology, can contain amino acid substitutions, deletions, or insertions. The substitutions can be conservative or non-conservative. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine.

In some embodiments, the C-peptide is a human C-peptide. An exemplary amino acid sequence for the human C-peptide is as follows: EAEDLQVGQVELGGGPGAGSLQPLALEGSLQ (SEQ ID NO:1). In some embodiments, the C-peptide is a porcine C-peptide. An exemplary sequence for porcine C-peptide is as follows: ELEDPQVEQTELGMGLGAGGLQPLALEMALQ (SEQ ID NO:2). In some embodiments, the C-peptide is a bovine C-peptide, e.g., one having the following amino acid sequence: EVEGPQVGALELAGGPGAGGLEGPPQ (SEQ ID NO:3).

In some embodiments, the C-peptide is a chicken C-peptide, e.g., comprising or consisting of the following amino acid sequence: DVEQPLVSSPLRGEAGVLPFQQEEYEKV (SEQ ID NO:4). In some embodiments, the C-peptide is from a zebrafish, e.g., having or consisting of the following sequence: DVEPLLGFLPPKSAQETEV ADFAFKDHAELI (SEQ ID NO:5).

In some embodiments, the C-peptide is a variant of a naturally-occurring C-peptide. For example, the C-peptide may, in some embodiments, consist of or comprise an amino acid sequence that is at least 70 (e.g., at least 75, 80, 85, 90, 95, or 99) % identical to the amino acid sequence depicted in any one of SEQ ID NOs:1-5. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software, such as BLAST software. Appropriate parameters for measuring alignment, including any algorithms needed to achieve maximal alignment over the full-length of the sequences being compared can be determined by known methods.

In some embodiments, the C-peptide comprises or consists of an amino acid sequence that has no more than 15 (e.g., no more than 14, 13, 12, 11, 10, 9, 8, 7, 6, 5, 4, 3, 2, or 1) amino acid substitutions, deletions, insertions, or a mixture of the above, relative to any one of SEQ ID NOs:1-5. The substitutions can be conservative, non-conservative, or a mixture of both. In some embodiments, the C-peptide is a fraction of a corresponding full length C-peptide having at least 5 amino acids of the sequence EGSLQ (SEQ ID NO:17).

As used herein, the term "conservative substitution" refers to the replacement of an amino acid present in the native sequence in a given polypeptide with a naturally or non-naturally occurring amino acid having similar steric properties. Where the side-chain of the native amino acid to be replaced is either polar or hydrophobic, the conservative substitution should be with a naturally occurring amino acid, a non-naturally occurring amino acid that is also polar or hydrophobic, and, optionally, with the same or similar steric properties as the side-chain of the replaced amino acid. Conservative substitutions typically include substitutions within the following groups: glycine and alanine; valine, isoleucine, and leucine; aspartic acid and glutamic acid; asparagine, glutamine, serine and threonine; lysine, histidine and arginine; and phenylalanine and tyrosine. One letter amino acid abbreviations are as follows: alanine (A); arginine (R); asparagine (N); aspartic acid (D); cysteine (C); glycine (G); glutamine (Q); glutamic acid (E); histidine (H); isoleucine (I); leucine (L); lysine (K); methionine (M); phenylalanine (F); proline (P); serine (S); threonine (T); tryptophan (W), tyrosine (Y); and valine (V).

The phrase "non-conservative substitutions" as used herein refers to replacement of the amino acid as present in the parent sequence by another naturally or non-naturally occurring amino acid, having different electrochemical and/or steric properties. Thus, the side chain of the substituting amino acid can be significantly larger (or smaller) than the side chain of the native amino acid being substituted and/or can have functional groups with significantly different electronic properties than the amino acid being substituted.

Variant forms of C-peptide retain at least 50 (e.g., at least 51, 52, 53, 54, 55, 56, 57, 58, 59, 60, 65, 70, 75, 80, 85, 90, 95, 99, or even 100) % of the activity (e.g., uptake by RBCs, delivery of $Zn^{2+}$ to RBCs, and/or stimulation of ATP release from RBCs) of the wild-type C-peptide from which they were derived. For example, a variant form of human C-peptide having three amino acid substitutions relative to SEQ ID NO: 1 would retain at least 50% of the ability of wild-type human C-peptide of SEQ ID NO: 1 to bind RBCs, delivery of $Zn^{2+}$ to RBCs, and/or stimulate ATP release from RBCs. Methods for measuring C-peptide binding to RBCs, uptake of C-peptide by RBCs, and/or ATP release by RBCs are known in the art and described and exemplified herein.

Methods for making C-peptide, including recombinant methods, are well known in the art. See, e.g., U.S. Pat. Nos. 6,558,924 and 8,691,755. C-peptide is also available from commercial sources, e.g., Sigma-Aldrich® (St. Louis, Mo.; product number C5051).

In some embodiments, a C-peptide can be modified, e.g., with a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag, e.g., FLAG (DYKDDDDK; SEQ ID NO:8), polyhistidine (6-His; HHHHHH; SEQ ID NO:6), hemagglutinin (HA; YPYDVPDY A; SEQ ID NO:7), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., 32P, 33P, 14C, 125I, 131I, 35 S, and 3H. Suitable fluorescent labels include, without limitation, fluorescein, fluorescein isothiocyanate (FITC), green fluorescent protein (GFP), DyLight™ 488, phycoerythrin (PE), propidium iodide (PI), PerCP, PE-Alexa Fluor® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two molecules can be cross-linked using any of a number of known chemical cross linkers. Examples of such cross linkers are those that link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyl-dithio) toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents that link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxy-succinimide ester), an amino group and a carboxyl group (e.g., 4-[p-azidosalicylamido]butylamine), and an amino group and a guanidinium group that is present in the side chain of arginine (e.g., p-azidophenyl glyoxal monohy-drate).

In some embodiments, a radioactive label can be directly conjugated to the amino acid backbone of a protein agent. Alternatively, the radioactive label can be included as part of a larger molecule (e.g., $^{125}$I in meta-[$^{125}$I]iodophenyl-N-hydroxysuccinimide ([$^{125}$I]miPNHS)) that binds to free amino groups to form meta-iodophenyl (miP) derivatives of relevant proteins (see, e.g., Rogers et al. (1997) *J Nucl Med* 38:1221-1229) or chelate (e.g., to 1,4,7,10-tetraazacyclodo-decane-1,4,7,10-tetraacetic acid (DOTA) or diethylene tri-amine pentaacetic acid (DTPA)) which is in turn bound to the protein backbone. Methods of conjugating the radioac-tive labels or larger molecules/chelates containing them to the antibodies or antigen-binding fragments described herein are known in the art. Such methods involve incubat-ing the proteins with the radioactive label under conditions (e.g., pH, salt concentration, and/or temperature) that facili-tate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NHS) ester or tetrafluorophenyl (TFP) ester moieties attached to the fluorophores. In some embodi-ments, the fluorophores can be conjugated to a heterobi-functional cross-linker moiety such as sulfosuccinimidyl-4-(N-maleimidomethyl)cyclohexane-1-carboxylate (sulfo-SMCC). Suitable conjugation methods involve incubating an antibody protein, or fragment thereof, with the fluoro-phore under conditions that facilitate binding of the fluoro-phore to the protein. See, e.g., Welch and Redvanly (2003) "Handbook of Radiopharmaceuticals: Radiochemistry and Applications," John Wiley and Sons (ISBN 0471495603).

In some embodiments, the heterologous moiety is joined to the C-peptide as a fusion protein (e.g., an antigenic tag useful for detection of uptake of tag-bearing C-peptide).

The present technology provides the results of experi-ments showing that albumin (from any one of several species) facilitates binding of C-peptide by RBCs and thus enhances the sensitivity of C-peptide binding-related assays. The improved methods are useful for, among other things, detecting increased binding of C-peptide by RBCs from MS patients as, e.g., a diagnostic or prognostic indicator.

C-Peptide Binding Facilitators

As discussed above, the methods and compositions of the present technology employ a C-peptide binding facilitator. As used herein, the term "C-peptide binding facilitator" refers to a component that facilitates binding of C-peptide on a cell, such "binding" being the transfer, uptake, or other association of C-peptide in (e.g., within the cell) or on (e.g., on the outer surface or in the cell membrane) a cell. Thus, "binding" may include association of C-peptide to an outer surface of a cell membrane, binding to a receptor expressed on a cell membrane, or uptake of into a cell. Accordingly, in various embodiments, binding effects an association of C-peptide with a cell such that if the cell is removed from a solution, the molecule or atom remains associated with the cell. As noted above, without limiting the function or scope of the present technology, it has been found that the binding of C-peptide is enhanced in the presence of a C-peptide binding facilitator and, in some situations, C-peptide does not bind to cells without use of a C-peptide binding facili-tator. Moreover, it has been discovered that, in some embodiments, the binding of C-peptide to the cells may be affected by the presence of a disease state or disorder in the subject from whom the cells are obtained.

A person of ordinary skill in the art can easily determine whether a component of interest is a "C-peptide binding facilitator" by combining the component of interest, C-pep-tide, and cells, such as cells that express Glut1, together to form a mixture, incubating the mixture for from about 1 minute to about 24 hours at a temperature of from about 5° C. to about 50° C., and determining whether a portion of the C-peptide binds to the cells. C-peptide binding to the cells can be performed by directly measuring C-peptide bound to the cells or C-peptide remaining in solution or indirectly measuring C-peptide bound to the cells or C-peptide remain-ing in solution, such as, for example, by measuring $Zn^{2+}$, $Fe^{2+}$, and/or $Cr^{3+}$ associated with the C-peptide.

C-peptide binding facilitators useful herein include albu-mins, leptin, collagen, and mixtures thereof. As used herein, the term "albumin" or "serum albumin" includes all forms of the globular proteins known as albumins, as well as albu-minoids, and variants thereof. Albumins among those useful herein may be native, naturally derived, synthetic or semi-synthetic, including albumins isolated from any species (and amino acid sequences for albumin proteins from a wide variety of species are known in the art and publicly acces-sible). Such albumin polypeptides may be derived from the tissues of humans or other animals, such as from whole blood or blood fractions obtained from human, cow, chicken or pig blood, or from the eggs of chickens or other fowl. In some embodiments, the human albumin has the amino acid sequence provided by SEQ ID NO:9. In some embodiments, the human albumin protein has the sequence provided by SEQ ID NO:10, which is a human albumin protein without its amino-terminal leader sequence.

In some embodiments, the albumin protein is a bovine albumin protein. In some embodiments, the bovine albumin protein comprises the amino acid sequence provided by SEQ ID NO:11. In some embodiments, the bovine albumin pro-tein comprises or consists of the amino acid sequence of SEQ ID NO:12, which lacks a propeptide/leader sequence.

In some embodiments, the albumin protein is a chicken albumin protein. In some embodiments, the chicken albumin protein comprises or consists of the amino acid sequence provided by SEQ ID NO:13. In some embodiments, the chicken albumin protein comprises or consists of the amino acid sequence provided by SEQ ID NO:14, which lacks the amino-termiano propeptide/leader sequence.

In some embodiments, the albumin protein is a porcine albumin protein. In some embodiments, the porcine albumin protein comprises or consists of the amino acid sequence provided by SEQ ID NO:15. In some embodiments, the porcine albumin protein comprises or consists of the amino acid sequence provided by SEQ ID NO:16, which lacks the amino-terminal propeptide/leader sequence.

In some embodiments, the albumin protein is a variant of a naturally-occurring albumin protein. For example, the albumin protein may, in some embodiments, consist of or comprise an amino acid sequence that is at least 70 (e.g., at least 75, 80, 85, 90, 95, or 99) % identical to the amino acid sequence depicted in any one of SEQ ID NOs:9-16. In some embodiments, the C-peptide comprises or consists of an amino acid sequence that has no more than 40 (e.g., no more than 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1) amino acid substitutions, deletions, insertions, or a mixture of the above, relative to any one of SEQ ID NOs:9-16. The substitutions can be conservative, non-conservative, or a mixture of both. It is understood that albumin proteins described herein can be from a natural source or be produced recombinantly. The albumin proteins can comprise, in some embodiments, a heterologous moiety (e.g., a detectable label), e.g., via fusion protein or chemical conjugation (see above).

A variant form of wild-type albumin proteins retain at least 50 (e.g., at least 51, 52, 53, 54, 55, 56, 57, 58, 59, 60, 65, 70, 75, 80, 85, 90, 95, 99, or even 100) % of the activity of the wild-type albumin protein from which it was derived. For example, a variant form of human albumin having 10 amino acid substitutions relative to SEQ ID NO:10 would retain at least 50% of the ability of wild-type human albumin of SEQ ID NO:10 to facilitate delivery of C-peptide to RBCs. Methods for measuring C-peptide binding to RBCs, binding of C-peptide by RBCs, and/or ATP release from RBCs are known in the art and described and exemplified herein.

Methods for making albumin protein, including recombinant methods, are well known in the art. See, e.g., U.S. Patent Application Publication No. 20120165509, European Patent No. 0319067, and International Patent Application Publication No. WO 2014/094406. Albumin from many species is also available from commercial sources, e.g., Sigma-Aldrich® (St. Louis, Mo.; product numbers A4503, A9511, and A1830).

Methods for Measuring C-Peptide Binding by Cells

As discussed above, the present technology provides in vitro methods for measuring the binding of C-peptide by cells, comprising incubating the cells with C-peptide and an albumin or other C-peptide binding facilitator. As referred to herein, "measuring" (or "determining") refers to a qualitative or quantitative process to detect or measure (e.g., quantitatively measure), directly or indirectly, the existence or degree of binding (as defined above) of C-peptide by a cell of interest. Such cells include cells obtained from any animal, preferably humans or another mammalian subject. In particular, as discussed below, such cells may be obtained from a human or other animal subject having, or suspected of having, disease disorder (e.g., MS or other immune-mediated disease) associated with C-peptide. The cells are preferably cells that express Glut1, such as RBCs, macrophages, neutrophils, or endothelial cells.

As referred to herein, "incubating" refers to the contacting of cells with the C-peptide and C-peptide binding facilitator, preferably under conditions that allow for binding (as defined above) C-peptide by the cells. In various embodiments, incubating comprises forming a C-peptide cellular mixture comprising the cells with one or both of the C-peptide and the C-peptide binding facilitator. The mixture may be an intimate admixture of cells, C-peptide and C-peptide binding facilitator, or other formulation by which the cells are in sufficient contact with the C-peptide and C-peptide binding facilitator so as to allow binding of the C-peptide by the cells.

In various embodiments, a C-peptide cellular mixture is incubated under conditions (from about 5° C. to about 50° C., e.g., room temperature, and/or for at least 1, 5, 10, 15, 20, 30, 45, 60, 90, 120 minutes, or from about 1 minute to about 24 hours) sufficient to allow binding and/or uptake of the C-peptide by the RBC forming an aqueous mixture. Following incubation, the RBCs (containing bound or internalized C-peptide) can be separated from the mixture (containing free C-peptide). Separation can be accomplished, e.g., by way of centrifugation. In some embodiments, the RBCs are diluted to a 7% hematocrit, which is approximately 780 million cells per milliliter, for incubation with the C-peptide. However, it is understood that other dilutions are acceptable, such as hematocrits of from about 2% to about 20%.

As noted above and further discussed below, the cells may be contacted with a known amount of C-peptide, so as to facilitate indirect determination of C-peptide binding by the cells through direct measurement of C-peptide remaining in solution after incubation (i.e., in the supernatant after the incubated cells are removed from the incubated C-peptide cellular mixture). Thus, a "known" amount is an amount of C-peptide that is quantified prior to formation of the C-peptide cellular mixture, such as by mixing a pre-determined amount of C-peptide with cells (and the C-peptide binding facilitator) to form the C-peptide cellular mixture.

In various embodiments, the method includes mixing from about 0.05 mL to about 20 mL, or from about 1 mL to about 5 mL of a cell suspension from a test subject (such as a red blood cell suspension having a hematocrit of from about 2% to about 20% or purified RBCs having a hematorcrit of from about 20% to about 90%) with from about 1 pmole to about 500 pmoles or from about 10 pmoles to about 50 pmoles of C-peptide, and from about 0.05% (w/v) to about 25% (w/v), or from about 1% (w/v) to about 10% (w/v) of a C-peptide binding facilitator. In another embodiment, cells, C-peptide, and a C-peptide binding facilitator are combined to generate an isotonic solution including the cells at a hematocrit of from about 2% to about 20%, from about 100 pM to about 1 mM or from about 500 pM to about 1000 nM C-peptide, and from about 0.05% (w/v) to about 25% (w/v), or from about 1% (w/v) to about 10% (w/v) of the C-peptide binding facilitator. The methods also includes incubating the isotonic solution at from about 5° C. to about 50° C. for from about 1 minute to about 24 hours and determining the amount of C-peptide bound to the cells. Obtaining RBCs from a subject (e.g., a human) is a routine procedure and well-known to those of skill in the art (e.g., using phlebotomy). For example, blood can be obtained from subjects by venipuncture using a syringe containing, e.g., citrate or heparin. Horn et al. (1995) *J Physiol* 489(1): 73-80. Isolated blood is then centrifuged at approximately 500 g at room temperature (about 20° C.) for 10 minutes, and the plasma, buffy coat, and uppermost layer of RBCs are removed by aspiration. The remaining RBCs can then be resuspended and, optionally, washed in a physiologic buffer, e.g., containing (in mM) 21.0 Tris, 4.7 KCl, 2.0 CaCl$_2$, 140.5 NaCl, 1.2 MgSO$_4$, 5.5 glucose, and 0.5% bovine serum albumin (BSA) with the pH adjusted to 7.4 (or other suitable buffer or wash solution). After the final wash, the hematocrit of the isolated RBCs can be measured. RBCs can be prepared on the day of use in the assay or stored until the day of use in the assay. See, e.g., Richards et al. (2013) *Am J Physiol Regul Integr Camp Physiol* 305(11):R862-868. In some embodiments, an assay is performed up to a step of separating cells from a supernatant and the supernatant is stored for further processing at a later time.

As noted above, determining the binding of C-peptide may be assessed by direct measurement of binding of C-peptide by cells, or indirectly such as through measuring the amount of C-peptide that is not bound by the cells relative to a known amount of C-peptide with which the cells are mixed to form the incubated cellular mixture. For example, measuring uptake and/or binding of C-peptide to RBCs can be accomplished, e.g., by detecting or otherwise measuring the amount of C-peptide bound to the RBCs, measuring or detecting the amount of free C-peptide remaining in the mixture, or, as described below, measuring the ATP release from the RBCs. In some embodiments, the amount of free C-peptide is measured against the starting amount of C-peptide added to the mixture. In some embodiments, the amount of C-peptide bound to, or internalized by, the RBCs can be detected or measured (e.g., by fluorescence-assisted cell sorting (FACS)/flow cytometry, or by lysis of the RBCs and detection or measurement of C-peptide associated with the lysate).

Methods for detecting or quantifying C-peptide (e.g., labeled or unlabeled C-peptide) are known in the art. For example, free C-peptide can be detected and/or quantified using a variety of techniques such as, but not limited to, BioLayer Interferometry (BLI), Western blot, dot blot, surface plasmon resonance method (SPR), enzyme-linked immunosorbent assay (ELISA), AlphaScreen® or AlphaLISA® assays, or mass spectrometry based methods. The capture or detection reagent can be, e.g., an antibody that binds to C-peptide (e.g., an epitope of C-peptide that is conserved across several species), an antibody that binds to an epitope tag (e.g., a flag, his, or HA tag, in embodiments in which a C-peptide comprising such a tag is used). Antibodies that bind to C-peptide are known in the art and described in, e.g., EP1191337 and U.S. Patent Application Publication No. 20050037448. Commercially available anti-C-peptide antibodies include, e.g., 5B8 (AbD Serotec®). Methods for making antibodies that bind to C-peptide are also well known in the art.

A variety of immunoassay techniques, including competitive and non-competitive immunoassays, can be used. The term "immunoassay" encompasses techniques including, without limitation, flow cytometry, FACS, enzyme immunoassays (EIA), such as enzyme multiplied immunoassay technique (EMIT), enzyme-linked immunosorbent assay (ELISA), IgM antibody capture ELISA (MAC ELISA) and microparticle enzyme immunoassay (MEIA), furthermore capillary electrophoresis immunoassays (CEIA), radio-immunoassays (RIA), immunoradiometric assays (IRMA), fluorescence polarization immunoassays (FPIA) and chemiluminescence assays (CL). If desired, such immunoassays can be automated.

Immunoassays can also be used in conjunction with laser induced fluorescence. Liposome immunoassays, such as flow-injection liposome immunoassays and liposome immunosensors, are also suitable for use in the present invention. In addition, nephelometry assays, in which, for example, the formation of protein/antibody complexes results in increased light scatter that is converted to a peak rate signal as a function of the marker concentration, are suitable for use in the methods of the present invention. In a preferred embodiment of the present invention, the incubation products are detected by ELISA, RIA, fluoro immunoassay (FIA) or soluble particle immune assay (SPIA).

Figure 3:
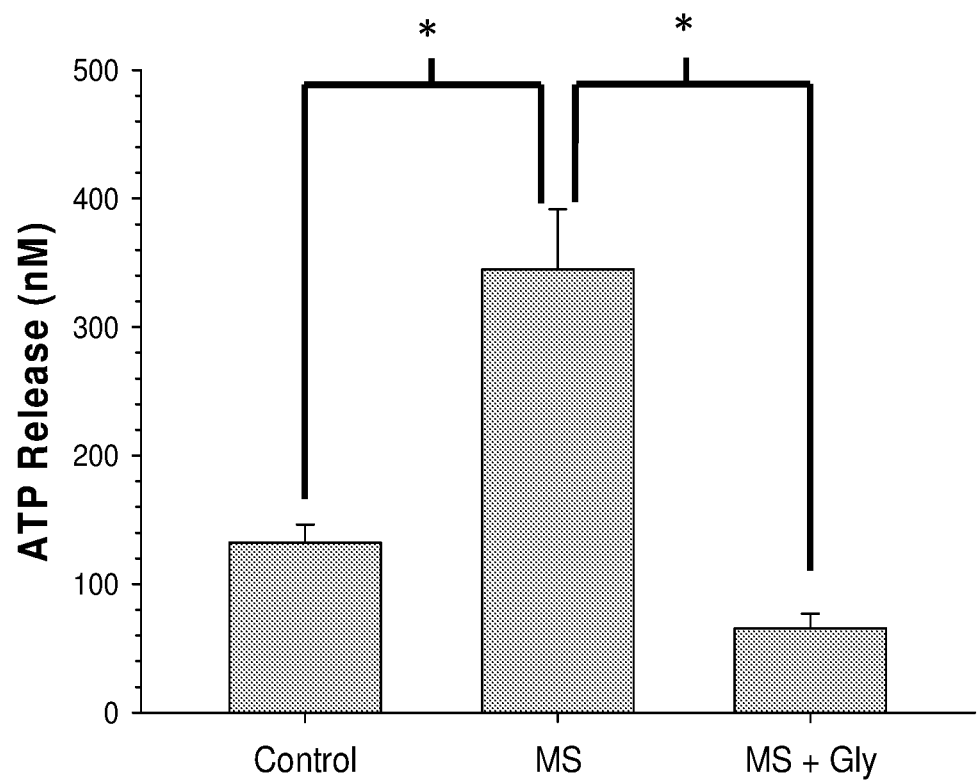

In some embodiments, detecting or measuring the amount of C-peptide uptake can be accomplished by measuring ATP release by the RBCs contacted with C-peptide (and, optionally, $Zn^{2+}$, $Fe^{2+}$, and/or $Cr^{3+}$). Methods for measuring ATP release by RBCs are known in the art and described in, e.g., Faris and Spence (2008) *Analyst* 133(5):678-682; Fischer et al. (2003) *Analyst* 128(9):1163-1168; Petruzzi et al. (1994) *Metabolism* 43(4):435-440; Richards et al. (2013) *Am J Physiol Regul Integr Comp Physiol* 305(11):R1331-1336; and Richards et al. (2014) *Am J Physiol Regul Integr Comp Physiol* 307(7):R862-868. For example, ATP can be measured using a luciferin-luciferase assay. RBCs contacted with C-peptide, albumin and $Zn^{2+}$, $Fe^{2+}$, and/or $Cr^{3+}$ can be added to a cuvette containing firefly lantern extract (e.g., 10 mg/ml distilled water, FLE 250; Sigma-Aldrich®, St. Louis, Mo.) and d-luciferin solution (e.g., 10 mg/20 ml distilled water; Research Products International, Mount Prospect, Ill.). The light emitted from the reaction with ATP can be quantified using a luminometer. A standard curve can be generated for each experiment and ATP values can be normalized to the amount released from a given number of cells. Richards et al. (2013) *Am J Physiol Regul Integr Comp Physiol* 305(11):R1331-1336. FIG. 3 shows a bar graph depicting results from an ATP release study.

Figure 4:
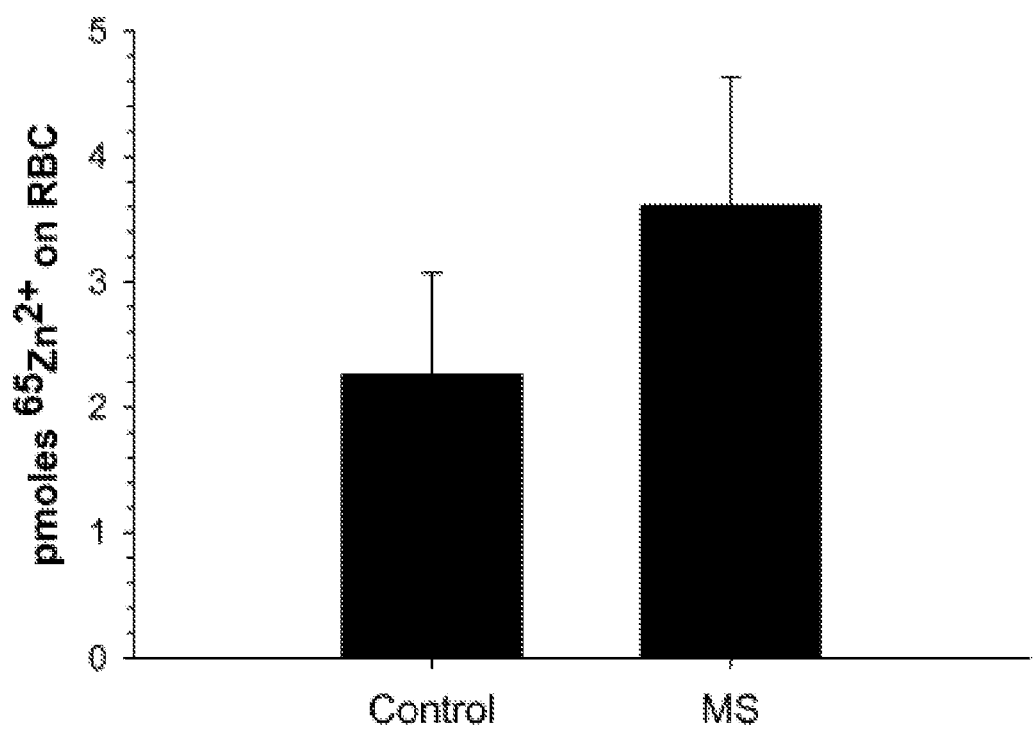

In some embodiments, e.g., those in which RBCs are contacted with C-peptide and $Zn^{2+}$, $Fe^{2+}$, and/or $Cr^{3+}$, in the presence of albumin or other C-peptide binding facilitator, $Zn^{2+}$, $Fe^{2+}$, and/or $Cr^{3+}$ uptake by RBCs can be measured (e.g., as a proxy for C-peptide uptake). Methods for detecting or measuring $Zn^{2+}$ uptake by RBCs are known in the art and described in, e.g., Horn et al. (1995) J Physiol 489(1): 73-80 (describing the use of radiolabeled $Zn^{2+}$). FIG. 4 shows a bar graph that shows a difference in $Zn^{2+}$ binding between control cells and cells from MS patients.

In various embodiments, the present technology provides methods for measuring C-peptide binding by cells. The method includes: contacting cells with a known amount of C-peptide and a C-peptide binding facilitator to form a C-peptide cellular mixture; incubating the C-peptide cellular mixture to produce incubated cells in an incubated cellular mixture; and determining the amount of C-peptide bound to the incubated cells. As discussed below, such methods can be used to analyze the risk of developing a disorder in a mammalian subject or to determine the likelihood that a mammalian subject has a disorder. Determining an amount of C-peptide bound to the incubated cells includes separating the incubated cells from the incubated cellular mixture, forming an incubated cell fraction and a supernatant; and measuring: (i) the amount of C-peptide in the incubated cellular fraction; or (ii) the amount of C-peptide in the supernatant; or (iii) the amount of C-peptide in the supernatant, and subtracting the amount of C-peptide in the supernatant from the known amount of C-peptide; or (iv) any combination of (i), (ii), and (iii).

All of the above embodiments are suitable for development into high-throughput platforms.

Diagnostic Methods

The present technology also provides methods for managing, or providing information for use in managing, the health care of human or other animal subjects. As discussed above, it has been found that binding of C-peptide by the cells of a human or other animal subject may be altered (e.g., increased) in some disease states or disorders. For example, it has been found that the binding of C-peptide by cells (e.g., RBCs) in subjects having MS is increased relative to the binding of C-peptide by cells in normal subjects (i.e., subjects not having MS). Accordingly, the present technology provides compositions and methods for use in detecting or diagnosing such diseases or disorders, and for use in the course of treatment of such diseases and disorders. Such methods include any of the methods for measuring C-peptide binding by cells described above and elsewhere in this disclosure.

Diseases and disorders among those for which the methods of this technology may be used include, in various embodiments, immune-mediated diseases and/or autoimmune diseases. As used herein, the term "immune-mediated disease" includes diseases and other disorders that are associated with an abnormal immunological response, including autoimmune diseases. As used herein, the term "autoimmune disease" means a disease resulting from an immune response against a self-tissue or tissue component, including both self-antibody responses and cell-mediated responses. Such diseases include organ-specific autoimmune diseases, in which an autoimmune response is directed against a single tissue, such as Crohn's disease, ulcerative colitis, myasthenia gravis, vitiligo, Graves' disease, Hashimoto's disease, Addison's disease and autoimmune gastritis and autoimmune hepatitis, and inflammatory demyelinating disorders. Autoimmune diseases also include non-organ specific autoimmune diseases, in which an autoimmune response is directed against a component present in several or many organs throughout the body. Such autoimmune diseases include, for example, rheumatoid disease, systemic lupus erythematosus, progressive systemic sclerosis and variants, polymyositis and dermatomyositis. Additional autoimmune diseases include pernicious anemia including some of autoimmune gastritis, primary biliary cirrhosis, autoimmune thrombocytopenia, Sjogren's syndrome, MS, and psoriasis. One skilled in the art understands that the methods of the invention can be applied to these or other autoimmune diseases, as desired. In various embodiments, the methods of the present technology are used in assessing an inflammatory demyelinating disorder, such as MS. In various embodiments, the MS is relapsing remitting MS or chronic progressive MS, e.g., primary-progressive, secondary progressive, or progressive relapsing MS.

For example, the present technology provides methods for assessing the status of an immune-mediated disease (e.g., MS) in a human or other animal subject. Such "assessing the status" includes methods to assess the risk of, diagnose, or monitor an immune-mediated disease associated with C-peptide in subjects having an immune-mediated disease or at risk of having an immune-mediated disease, as well as to provide information useful in such assessment, diagnosis or monitoring.

In some embodiments of any of the methods described herein, the subject is one suspected of having an immune-mediated disease or at risk for developing an immune-mediated disease. In some embodiments, the subject is suspected of having, or is at risk for developing, MS. In some embodiments, any of the methods described herein can be used to assess the status (e.g., diagnose) of an immune-mediated disease in a subject as having an immune-mediated disease (e.g., MS), even when the subject is in clinical remission (e.g., smoldering disease).

Accordingly, the present technology provides methods for assessing the probability that a mammalian subject has an immune-mediated disease. The methods includes contacting cells (e.g., RBCs) from a subject with a detection reagent in a constricted environment, such that the RBCs release ATP and the detection reagent facilitates detection of the ATP. RBCs from mammalian subjects that have an immune-mediated disease or are at risk of developing an immune-mediated disease, such as MS, release at least 2 fold more ATP relative to RBCs from normal mammalian subjects that do not have an immune-mediated disease or are not at risk of developing an immune-mediated disease. No C-peptide is required for this particular method. Accordingly, blood from a mammalian subject that generates greater than or equal to 2 fold more ATP relative to ATP released from normal blood obtained from a normal subject that does not have and is not at risk of developing an immune-mediated disease indicates a high probability that the mammalian subject has an immune-mediated disease, such as MS.

In other aspects, the present technology provides methods for diagnosing a disorder, such as MS, in a mammalian subject, comprising obtaining cells from the subject and performing an in vitro method for measuring the binding of C-peptide by cells according to the present technology. Also provided are methods for analyzing the risk of developing a disorder, such as MS, in a mammalian subject, comprising obtaining cells from the subject and performing an in vitro method for measuring the binding of C-peptide by cells according to the present technology. Also provided are methods, for determining the likelihood that a mammalian subject has a disorder, such as MS, comprising obtaining cells from the subject and performing an in vitro method for measuring the binding of C-peptide by cells according to the present technology.

In various embodiments, the present technology provides in vitro methods for assessing the probability that a mammalian subject has an immune-mediated disease, the method comprising:

incubating cells that express Glut1 obtained from the subject with a C-peptide composition comprising an amount, e.g., a known amount, of C-peptide and an albumin under conditions that allow for the cells to bind the C-peptide to form incubated cells in an incubated cellular mixture;

separating the incubated cells from the incubated cellular mixture; and determining the amount of C-peptide bound to the incubated cells. As discussed above, in various embodiments, determining the binding of C-peptide may be assessed by direct measurement of binding of C-peptide by cells, or indirectly such as through measuring the amount of C-peptide that is not bound by the cells.

In various embodiments, a C-peptide binding of greater than or equal to about 2000, greater than or equal to about 2100, greater than or equal to about 2200, greater than or equal to about 2300, greater than or equal to about 2400, greater than or equal to about 2500, greater than or equal to about 2600, greater than or equal to about 2700, greater than or equal to about 2800, greater than or equal to about 2900, or greater than or equal to about 3000 C-peptide molecules per cell indicates a high probability that the test subject has an immune-mediated disease, such as MS. In other embodiments, a C-peptide binding of from about 2300 to about 2800 C-peptide molecules per cell indicates a high probability that the test subject has an immune-mediated disease, such as MS. C-peptide binding in healthy individuals that do not have MS is about 1500 C-peptide molecules per cell.

As referred to herein, such methods of "assessing the probability" provide information that may be useful by a health care provider (e.g., physician) in diagnosing, monitoring or treating a subject as currently having, or being at risk of having, an immune-mediated disease. In some embodiments, a method for assessing the probability is performed by a technician or other medical practitioner (e.g., in a diagnostic laboratory), providing information regarding the amount of C-peptide bound to incubated cells which is then used by a physician or other health care provider to diagnose, monitor or treat a subject having, or at risk of having, an immune-mediated disease. Such information may be used, together with other diagnostic information, to determine whether a subject actually has the immune-mediated disease or whether the subject is at risk of developing the immune-mediated disease. Thus, in some embodiments, the methods of the present technology further comprise receiving a request, e.g., by a diagnostic technician from a physician or other health care provider, to determine whether a subject has an immune-mediated disease.

Thus, in some embodiments, the present technology provides methods for determining whether a subject has an immune-mediated disease, such as MS. An exemplary method for detecting the amount involves, optionally, obtaining RBCs from a subject and contacting the red bloods, in the presence of albumin or other C-peptide binding facilitator (and optionally $Zn^{2+}$, $Fe^{2+}$, and/or $Cr^{3+}$), with a C-peptide, such as a human C-peptide, and: (1) detecting or measuring the amount of C-peptide bound to the RBCs, (2) measuring or detecting the amount of free C-peptide remaining in the mixture; (3) detecting or measuring the ATP release from the RBCs; and/or (4) detecting or measuring $Zn^{2+}$, $Fe^{2+}$, and/or $Cr^{3+}$ uptake by the RBCs. An increased amount of C-peptide uptake by the RBCs, a reduced amount of free C-peptide, an increase in ATP release by RBCs, and/or an increase in $Zn^{2+}$, $Fe^{2+}$, and/or $Cr^{3+}$ uptake by the RBCs, indicates that the subject has an immune-mediated disease.

In some embodiments, the amount of C-peptide bound to the incubated cells is compared to a reference amount determined by performing the incubating, separating and determining using cells obtained from a second subject that does not have the immune-mediated disease. In some embodiments, an amount of C-peptide bound to the incubated cells greater than or equal to about a factor of from about 1.2 to about 5 fold (e.g., about 1.5 fold) relative to the reference amount is indicative of a high probability of the subject currently having the immune-mediated disease In some embodiments, an increase in C-peptide uptake of at least 10 (e.g., at least 15, 20, 25, 30, 35, 40, 45, 50, 55, 60, 65, 70, 75, 80, 85, 90, 95, 100, or more than 100)% over a normal control level (e.g., normal control C-peptide uptake level) indicates that the subject has an immune-mediated disease. In some embodiments, an increase in C-peptide uptake of at least 1.5 (e.g., at least 2, 3, 4, 5, 6, 7, 8, 9, 10, 20, 30, 40) fold over a normal control level (e.g., normal control C-peptide uptake level) indicates that the subject has an immune-mediated disease.

The term "control" refers to any reference standard suitable to provide a comparison to the test sample. As described above, the methods described herein can involve comparing the C-peptide binding, remaining free C-peptide, $Zn^{2+}$, $Fe^{2+}$, and/or $Cr^{3+}$ uptake, or ATP release to a control amount. In some embodiments, the control is a control sample obtained from a normal, healthy subject of the same species who does not have, is not suspected of having, and/or is not at risk for developing an immune-mediated disease, such as, for example, MS. In some embodiments, the control can be (or can be based on), e.g., a collection of samples obtained from two or more (e.g., two, three, four, five, six, seven, eight, nine, 10, 15, 20, 25, 30, 35, or 40 or more) healthy individuals (e.g., a mean or median level). In some embodiments, the control can be (or can be based on), e.g., one sample or a collection of samples obtained from two or more (e.g., two, three, four, five, six, seven, eight, nine, 10, 15, 20, 25, 30, 35, or 40 or more) individuals (e.g., a mean or median level) determined to be in clinical remission of an immune-mediated disease (e.g., MS). In some embodiments, the control amount is detected or measured concurrently with the test sample. In some embodiments, the control level or amount is a pre-determined range or threshold based on, e.g., average levels from a control group (e.g., normal healthy volunteer subjects). Thus, a normal control C-peptide uptake level can be the C-peptide uptake level determined from a RBCs obtained from a healthy subject of the same species. A normal control C-peptide uptake level can be the mean, or a range of values around the mean, of obtained from C-peptide uptake measurements from two or more normal healthy subjects of the same species as the subject of interest. In some embodiments, the normal control C-peptide uptake level is a threshold value (e.g., determined based on the average C-peptide uptake levels from subjects with a particular immune-mediated disease, e.g., MS) or a particular form of an immune-mediated disease (secondary progressive MS), above which indicates that a subject has an immune-mediated disease.

In some embodiments, the control is a control sample obtained from a subject of the same species who has, is suspected of having, and/or is at risk for developing an immune-mediated disease (e.g., immune-mediated disease, such as MS). In some embodiments, the control can be (or can be based on), e.g., a collection of samples obtained from two or more (e.g., two, three, four, five, six, seven, eight, nine, 10, 15, 20, 25, 30, 35, or 40 or more) individuals of the same species (e.g., a mean or median level) who have an immune-mediated disease. Thus, an MS control C-peptide uptake level can be the C-peptide uptake level determined from RBCs obtained from a subject of the same species who has MS. An MS control C-peptide uptake level can be the mean, or a range of values around the mean, of obtained from C-peptide uptake measurements from two or more immune-mediated disease-afflicted subjects of the same species as the subject of interest.

The methods of the present invention are not limited to use of a specific cut-point in comparing a level (e.g., C-peptide uptake level) in the test sample to the control. Without limiting the scope or function of the present technology, this may be seen, for example, from the data presented below.

In some embodiments, the methods further involve obtaining a control biological sample (e.g., biological sample from a subject who does not have an immune-mediated disease) or a biological sample from the subject during treatment to monitor the regression or further progression of the immune-mediated disease.

In some embodiments, the methods described herein can be used to determine whether a subject with an immune-mediated disease is responsive to treatment, as further described below. For example, C-peptide can be incubated, in the presence of a C-peptide binding facilitator (e.g., albumin), with cells (e.g., RBCs) from a subject under conditions that allow for binding of C-peptide by RBCs, wherein the subject has an immune-mediated disease, such as MS, and is being treated with an immunosuppressant or anti-inflammatory agent; and determining the amount of binding of C-peptide by the RBCs, wherein decreased binding of C-peptide by the RBCs, relative to a control C-peptide uptake level (e.g., an MS control C-peptide uptake level), indicates that the subject is responsive to treatment with the immunosuppressant or the anti-inflammatory agent. (One of skill in the art would appreciate based on the present technology that variations of such a method involving $Zn^{2+}$, $Fe^{2+}$, and/or $Cr^{3+}$ uptake and/or ATP release would also be useful for monitoring responsiveness.)

In addition to monitoring disease progression using the methods described herein, an MS therapy, e.g., can be deemed to be effective if there is a statistically significant difference in the rate or proportion of exacerbation-free or relapse-free patients between the treated group and the placebo group for either of these measurements. In addition, time to first exacerbation and exacerbation duration and severity may also be measured. A measure of effectiveness as therapy in this regard is a statistically significant difference in the time to first exacerbation or duration and severity in the treated group compared to control group. An exacerbation-free or relapse-free period of greater than one year, 18 months, or 20 months is particularly noteworthy.

Clinical measurements include the relapse rate in one and two-year intervals, and a change in EDSS (expanded disability status scale), including time to progression from baseline of 1.0 unit on the EDSS that persists for six months. On a Kaplan-Meier curve, a delay in sustained progression of disability shows efficacy. Other criteria include a change in area and volume of T2 images on MRI, and the number and volume of lesions determined by gadolinium enhanced images. MRI can be used to measure active lesions using gadolinium-diethylenetriamine pentaacetic acid (DTPA)-enhanced imaging (McDonald et al., Ann. Neurol. 36:14, 1994) or the location and extent of lesions using T2-weighted techniques. Briefly, baseline MRIs are obtained. The same imaging plane and patient position are used for each subsequent study. Positioning and imaging sequences can be chosen to maximize lesion detection and facilitate lesion tracing. The same positioning and imaging sequences can be used on subsequent studies. The presence, location and extent of MS lesions can be determined by radiologists. Areas of lesions can be outlined and summed slice by slice for total lesion area. Three analyses may be done: evidence of new lesions, rate of appearance of active lesions, percentage change in lesion area (Paty et al. (1993) Neurology 43:665). Improvement due to therapy can be established by a statistically significant improvement in an individual patient compared to baseline or in a treated group versus a placebo group.

The present technology also provides in vitro methods for diagnosing a mammalian subject as having an immune-mediated disease, the method comprising:
  incubating, in the presence of albumin, RBCs from the subject with C-peptide under conditions that allow for binding of C-peptide by RBCs; and
  determining the amount of C-peptide bound by the RBCs, wherein increased binding of C-peptide by the RBCs, relative to a control C-peptide binding level, indicates that the subject has the immune-mediated disease.

In various embodiments, the immune-mediated disease is an inflammatory demyelinating disorder, such as MS. In some aspects, such in vitro methods for diagnosing a subject as having an immune-mediated disease. Such method comprise: contacting, in the presence of albumin, RBCs from a subject of interest with C-peptide to form a mixture; incubating the mixture under conditions that allow for binding of C-peptide by RBCs; and determining the amount of binding of C-peptide by the RBCs. An increased binding of C-peptide by the RBCs, relative to a control C-peptide uptake level (e.g., a normal control C-peptide uptake level), indicates that the subject has an immune-mediated disease.

In some embodiments, in vitro methods for diagnosing a subject as having an immune-mediated disease, comprise: contacting, in the presence of albumin, RBCs from a subject of interest with C-peptide to form a mixture; incubating, in the presence of albumin, RBCs from a subject of interest with C-peptide under conditions that allow for binding of C-peptide by RBCs; contacting free C-peptide with an agent that specifically binds to the free C-peptide to form an agent-C-peptide complex; and applying a detection reagent that detects the agent-C-peptide complex to thereby determine the amount of free C-peptide, wherein a decreased amount of free C-peptide, relative to a control free C-peptide level (e.g., a normal control free C-peptide level), indicates that the subject has an immune-mediated disease.

In some embodiments, in vitro methods for diagnosing a subject as having MS comprise: incubating, in the presence of albumin, RBCs from a subject of interest with C-peptide under conditions that allow for binding of C-peptide by RBCs; and determining the amount of uptake of C-peptide by the RBCs, wherein increased binding of C-peptide by the RBCs, relative to a normal control C-peptide uptake level, indicates that the subject has MS.

The present technology also provides methods for effecting an assessment of the status of an immune-mediated disease (e.g., MS). Such effected methods include those of the present technology associated with the management of an immune-mediated disease, e.g., methods for analyzing the risk of developing a disorder, methods for diagnosing a disorder, and methods for determining the likelihood that a subject has a disorder, as described above. As referred to herein, such "effecting" includes performing such methods, or causing such methods to be performed. Thus, in some embodiments, effecting such methods may be performed by a physician or other health care professional directly or indirectly, wherein (for example) the in vitro a method for measuring the binding of C-peptide by cells according to the present technology is performed by another health care provider such as a diagnostic lab.

Methods of Treatment

Also provided herein are methods for treating a subject having an immune-mediated disease comprising performing or effecting an in vitro method of measuring the C-peptide binding of cells according to the present technology. Such methods comprise may one or more methods for management of an immune-mediated disease, e.g., methods for analyzing the risk of developing a disorder, methods for diagnosing a disorder, and methods for determining the likelihood that a subject has a disorder, as described above.

In various embodiments, such methods for treating an immune-mediated disease comprise methods of treating such disorders among those known in the art. For example, a medical professional can administer to a subject an anti-inflammatory compound or an immunosuppressant in an amount effective to treat an immune-mediated disease, wherein the subject has been diagnosed as having the immune-mediated disease by any of the in vitro methods described herein. In some embodiments, the professional can request the results of a test used to determine whether the subject has an immune-mediated disease, which test is, or includes, one of the in vitro methods for measuring C-peptide binding described herein. In some embodiments, the subject has been diagnosed as having MS. In some embodiments, the subject has been diagnosed as having relapsing-remitting MS, secondary progressive MS, primary progressive MS, or progressive relapsing MS. As used herein, a subject can be a human, a non-human primate (e.g., monkey, baboon, or chimpanzee), a horse, a cow, a pig, a sheep, a goat, a dog, a cat, a rabbit, a guinea pig, a gerbil, a hamster, a rat, or a mouse. In some embodiments, the mammal is an infant (e.g., a human infant).

As used herein, a subject "in need of prevention," "in need of treatment," or "in need thereof," refers to one, who by the judgment of an appropriate medical practitioner (e.g., a doctor, a nurse, or a nurse practitioner in the case of humans; a veterinarian in the case of non-human mammals), would reasonably benefit from a given treatment.

The term "preventing" is art-recognized, and when used in relation to a condition, is well understood in the art, and includes administration of a composition which reduces the frequency of, or delays the onset of, symptoms of a medical condition in a subject mammal relative to a subject which does not receive the composition.

As used herein, a subject "at risk for developing" an immune-mediated disease is a subject having one or more (e.g., two, three, four, five, six, seven, or eight or more) risk factors for developing an immune-mediated disease. A subject "suspected of having" an immune-mediated disease is one having one or more symptoms of the immune-mediated disease. It should be understood that mammal at risk for developing, or suspected of having, an immune-mediated disease does not include all mammals within the species of interest.

Exemplary symptoms associated with MS, which can be treated with the methods described herein, include: optic neuritis, diplopia, nystagmus, ocular dysmetria, internuclear ophthalmoplegia, movement and sound phosphenes, afferent pupillary defect, paresis, monoparesis, paraparesis, hemiparesis, quadraparesis, plegia, paraplegia, hemiplegia, tetraplegia, quadraplegia, spasticity, dysarthria, muscle atrophy, spasms, cramps, hypotonia, clonus, myoclonus, myokymia, restless leg syndrome, footdrop, dysfunctional reflexes, paraesthesia, anaesthesia, neuralgia, neuropathic and neurogenic pain, proprioceptive dysfunction, trigeminal neuralgia, ataxia, intention tremor, dysmetria, vestibular ataxia, vertigo, speech ataxia, dystonia, dysdiadochokinesia, bladder spasticity, flaccid bladder, detrusor-sphincter dyssynergia, erectile dysfunction, frigidity, constipation, fecal urgency, fecal incontinence, depression, cognitive dysfunction, dementia, mood swings, emotional lability, euphoria, bipolar syndrome, anxiety, aphasia, dysphasia, fatigue, uhthoff s symptom, gastroesophageal reflux, and sleeping disorders. See, e.g., International Patent Application Publication No. 2006/055871.

Suitable therapeutics for treating immune-mediated diseases include those known in the art. For example, treatments for MS include an anti-alpha 4 integrin antibody, interferon-beta-1a (e.g., Avonex®, Rebif®), Cinno Vex), or a derivative of interferon-beta-1a. Suitable therapies also include, but are not limited to, natalizumab (Tysabri®), peginterferon (Plegridy™), glatiramer acetate (Copaxone®), fingolimod (Gilenya®), or alemtuzumab (Campath®). Any of the methods described herein can also include treatments, such as interferon beta-1b (Betaseron®), mitoxantrone (Novantrone®), teriflunomide (Aubagio®), and dimethyl fumarate (BG 12, Tecfidera®).

The compositions described herein can be administered to a subject, e.g., a human subject, using a variety of methods that depend, in part, on the route of administration. The route can be, e.g., intravenous injection or infusion (IV), subcutaneous injection (SC), intraperitoneal (IP) injection, or intramuscular injection (IM).

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

As used herein the term "effective amount" or "therapeutically effective amount", in an in vivo setting, means a dosage sufficient to treat, inhibit, or alleviate one or more symptoms of the disorder being treated or to otherwise provide a desired pharmacologic and/or physiologic effect (e.g., modulate (e.g., enhance) an immune response to an antigen. The precise dosage will vary according to a variety of factors such as subject-dependent variables (e.g., age, immune system health, etc.), the disease, and the treatment being effected. Therapeutically effective amounts of the agents disclosed herein enhance an immune response by a mammal to a target antigen. Suitable human doses of any of the antibodies or fragments thereof described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10):3499-3500.

Toxicity and therapeutic efficacy of such compositions can be determined by known pharmaceutical procedures in cell cultures or experimental animals (e.g., animal models of cancer, vaccination, or infection). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Agents that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such antibodies or antigen-binding fragments thereof lies generally within a range of circulating concentrations of the antibodies or fragments that include the $ED_{50}$ with little or no toxicity. The dosage may vary within this range depending upon the dosage form employed and the route of administration utilized. A therapeutically effective dose can be estimated initially from cell culture assays. A dose can be formulated in animal models to achieve a circulating plasma concentration range that includes the $IC_{50}$ (i.e., the concentration of the antibody which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration is desired, cell culture or animal modeling can be used to determine a dose required to achieve a therapeutically effective concentration within the local site.

Accordingly, in various embodiments, the present technology provides methods for treating a subject having an immune-mediated disease, comprising administering to the subject an anti-inflammatory compound or an immunosuppressant in an amount effective to treat the immune-mediated disease, wherein the subject has been diagnosed as having the immune-mediated disease by any of the in vitro methods described herein. In another aspect, the present technology features a method for treating a subject having an immune-mediated disease. The method comprises: (i) requesting the results of a test to determine whether the subject has an immune-mediated disease, which test utilizes any of the in vitro methods described herein; and (ii) administering to the subject an anti-inflammatory compound or an immunosuppressant in an amount effective to treat the immune-mediated disease, if the results of the test indicate that the subject has an immune-mediated disease, such as MS.

In some embodiments, the present technology provides methods for determining whether a subject with MS is responsive to a treatment for MS, comprising: incubating, in the presence of albumin, RBCs from a subject with C-peptide under conditions that allow for binding of C-peptide by RBCs, wherein the subject has MS and is being treated with an immunosuppressant or anti-inflammatory agent; and determining the amount of binding of C-peptide by the RBCs, wherein decreased binding of C-peptide by the RBCs, relative to a control C-peptide uptake level (e.g., an MS control C-peptide uptake level), indicates that the subject is responsive to treatment with the immunosuppressant or the anti-inflammatory agent.

In various embodiments, the present technology provides methods of managing MS in a subject in need thereof, the method comprising:
(a) effecting an assay for measuring C-peptide binding on cells obtained from the subject, the assay comprising
  (i) incubating the cells with a C-peptide composition comprising a known amount of C-peptide and a C-peptide binding facilitator to produce incubated cells in an incubated cellular mixture; and
  (ii) determining the amount of C-peptide bound to the incubated cells.
(b) comparing the amount of C-peptide bound by the cells to a reference amount determined by performing the assay on cells obtained from a second subject that does not have the immune-mediated disease;
(c) administering a first treatment for MS; and
(d) assessing the efficacy of the administering by repeating the effecting and comparing.
In some embodiments, such methods further comprise administering a second treatment of MS after the assessing, wherein the second treatment is altered from the first treatment based on the results of the assessing. The present technology also provides methods of assessing the responsiveness of a mammalian subject having MS to a treatment for the MS.

Kits

Figure 2:
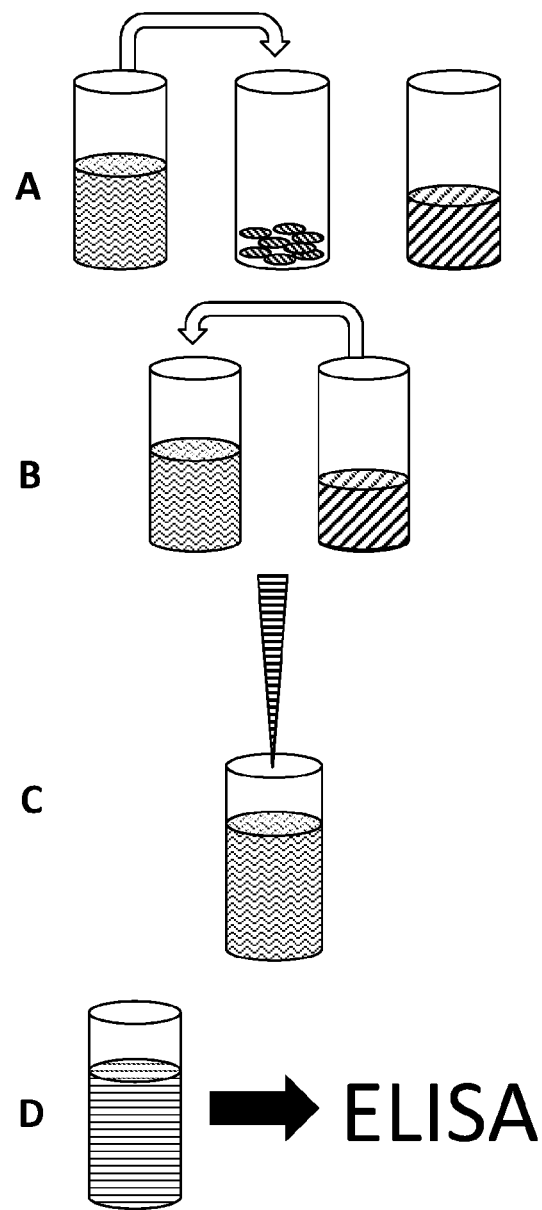

The present technology also provides kits for use in the methods of the present technology, as well as methods for using such kits. In various embodiments, such a "kit" is any manufacture (e.g., a package or container) comprising at least one reagent, e.g., an albumin protein, an C-peptide (e.g., detectably-labeled C-peptide), $Zn^{2+}$, $Fe^{2+}$, and/or $Cr^{3+}$ (e.g., solid or an aqueous solution of $ZnCl_2$), or an antibody that binds to C-peptide, for detecting C-peptide binding, free C-peptide, $Zn^{2+}$, $Fe^{2+}$, and/or $Cr^{3+}$ binding, or ATP release, e.g., for the diagnosis of an immune-mediated disease. In some embodiments, the present technology provides kits for use measuring C-peptide binding by cells, the kit comprising a C-peptide binding facilitator, C-peptide, and a container. In various embodiments, a kit may be promoted, distributed, or sold as a unit for performing the methods of the present invention. FIG. 2 shows an exemplary kit composition according to the present technology.

In some embodiments, the container is operable for mixing a solvent with one or both of the C-peptide binding facilitator and the C-peptide, and may be operable for mixing one or both of the C-peptide binding facilitator and the C-peptide with a suspension of cells.

In some embodiments, the container is a first container containing the C-peptide binding facilitator, and the kit further comprises a second container containing C-peptide. The kit may further comprise a third container containing a solvent for one or both of the C-peptide binding facilitator and the C-peptide. In some embodiments, one or both of the C-peptide and the C-peptide binding facilitator are in powder form, preferably as lyophilized powders. The solvent may comprise phosphate buffered saline, physiological saline solution, Tris buffer, or phosphate buffer. In some embodiments, a kit comprises a fourth container, wherein components of the first, second and third containers are mixed, optionally with a suspension of cells. In some aspects, the kits are used in methods comprising transferring a predetermined volume of the solvent in the third container to one of the first container or the second container and dissolving the contents of the first container or the second container in the solution to form a first working solution;

transferring the partial working solution to the other of the first container or the second container and dissolving the contents of the other of the first container or the second container to form a second working solution;

incubating a suspension of the cells with the second working solution to generate a C-peptide cellular mixture under conditions that allow for the cells to bind the C-peptide.

In certain embodiments, the kit may further comprise a reference standard (normal RBCs) and/or one or more suitable buffers (e.g., phosphate buffered saline or other physiological buffers). Reagents in the kit may be provided in individual containers or as mixtures of two or more reagents in a single container. In some embodiments, the kits include at least two containers, wherein one container comprises C-peptide (e.g., detectably-labeled C-peptide) and at least one container comprises albumin. In some embodiments, the kit comprises a container comprising $Zn^{2+}$, $Fe^{2+}$, and/or $Cr^{3+}$. Albumin or C-peptide can be provided in aqueous form or lyophilized. In some embodiments, the kits comprise one or more buffers for use in rehydrating a lyophilized product. In addition, instructional materials which describe the use of the compositions within the kit can be included.

In some embodiments, the kit comprises a device that is operable for obtaining RBCs from a subject (e.g., a syringe or a lancet). In some embodiments, the kit may comprise an analytical device or reagent for detecting or measuring C-peptide, such as an anti-C-peptide antibody or an antibody that binds to a specific epitope tag, where the C-peptide is epitope-tagged, such as discussed above.

Reagents

The present technology also provides reagents for use in measuring C-peptide binding to cells, such as cells that express Glut1. In some embodiments, a reagent consists essentially of peptide binding facilitator (e.g., albumin), dissolved in an isotonic solution and, optionally, further consisting of an optional component selected from the group consisting of C-peptide, a buffering agent, $Zn^{2+}$, $Fe^{2+}$, $Cr^{3+}$, and mixtures thereof. In some embodiments, a reagent consists essentially of C-peptide dissolved in an isotonic solution and, optionally, further consisting of an optional component selected from the group consisting of a C-peptide binding facilitator (e.g., albumin), a buffering agent, $Zn^{2+}$, $Fe^{2+}$, $Cr^{3+}$, and mixtures thereof.

Reagents may include a sufficient amount of C-peptide, such that from about 1 pmole to about 50 pmoles of the C-peptide in the reagent contact cells when the reagent is combined with the cells. Reagents may also include, or alternatively include, a sufficient amount of C-peptide binding facilitator, such that from about 0.05% (w/v) to about 10% (w/v) of the C-peptide binding facilitator in the reagent contact cells when the reagent is combined with the cells. In various embodiments, a reagent includes from about 100 pM to about 1 mM C-peptide and from about 0.05% (w/v) to about 25% (w/v) C-peptide binding facilitator, as described above. The reagent may also include a buffering agent, such as piperazine-N,N'-bis(2-ethanesulfonic acid) (PIPES), (3-(N-morpholino)propanesulfonic acid) (MOPS), (4-(2-hydroxyethyl)-1-piperazineethanesulfonic acid) (HEPES), 2-[(2-Hydroxy-1,1-bis(hydroxymethyl)ethyl)amino]ethanesulfonic acid (TES), tris(hydroxymethyl)aminomethane (TRIS), tris(hydroxymethyl)aminomethane hydrochloride (TRIS-HCL), N-[Tris(hydroxymethyl)methyl]glycine (TRICINE), 3-[4-(2-Hydroxyethyl)-1-piperazinyl]propanesulfonic acid (HEPPS), N,N-Bis(2-hydroxyethyl)glycine (BICINE), N-[Tris(hydroxymethyl)methyl]-3-aminopropanesulfonic acid (TAPS), or phosphate as non-limiting examples. Such buffering agents, and others, are known in the art.

EXAMPLES

The following examples are meant to illustrate, not to limit, the present technology.

Example 1

The amount of C-peptide binding to RBCs obtained from MS patients was compared to controls run on the same day. All samples were handled in an identical manner. Briefly, about 10 mL of blood were drawn from each donor; the RBCs were purified by centrifugation. Next, 20 picomoles of human C-peptide were added to a buffer containing 75 micromolar albumin. RBCs were added to this C-peptide and albumin-containing buffer and allowed to incubate for 2 hours. Next, the samples were centrifuged and the moles of C-peptide remaining in the supernatant are subtracted from the original amount added. This provided a value corresponding to the moles of C-peptide bound to the RBCs. FIG. 1 shows the average amount of C-peptide bound to the RBCs obtained from patients with MS and healthy controls. Importantly, of the 25 MS patient samples analyzed, the values ranged from 2.7 to 4.8 picomoles of C-peptide bound to the RBCs, with 18 of the 25 above 3.2 picomoles. In comparison, one control was 3.1, another was 2.8; all others were below 2.45. Thus, separation exists between groups—approximately 2.7 picomoles of bound C-peptide difference.

Additional samples from healthy controls and MS patients were analyzed for C-peptide binding, ATP release (10 healthy control patients, 10 MS patients, and 12 MS patients with glybenclamide), and $Zn^{2+}$ binding (11 healthy control patients and 22 MS patients). The ATP release from the RBCs of MS patients was found to be an average of 344.7±46.8 nM where the average release from healthy controls was 132.1±14.1 nM. As shown in FIG. 4, the amount of $^{65}Zn^{2+}$ that is able to interact with the RBCs of MS patients is significantly higher, at a value of 3.61±0.22 picomoles, than that of healthy controls, at a value of 2.26±0.24 picomoles. Here, 20 nM $^{65}Zn^{2+}$ was incubated with the RBCs and 20 nM C-peptide. It is noteworthy that in 32 of these 34 samples, MS ATP release, C-peptide and/or $Zn^{2+}$ binding, was higher than the control samples analyzed simultaneously with the MS samples.

Similar studies were performed using serum albumin from other species (human, porcine, chicken); all of these forms deliver C-peptide to RBCs and are useful in the methods described herein.

Example 2

The amount of C-peptide binding to RBCs obtained from 86 MS patients and 75 patients diagnosed with a non-MS neurological disease (OND) was compared to controls blood from 39 patients without MS or OND in a binding experiment (to demonstrate a diagnostic test).

The MS patients were 75% female and ages ranged between all the MS patients from 21-81 years (52 years average). The MS patients had the disease for an average of 13.9 years. 24% of the patients were not on any disease-modifying therapy.

The OND patients were 46% female and ages ranged between all the OND patients from 21-88 years (63 years average). OND diseases include myasthenia gravis, brain tumor, optic neuropathy, sixth nerve palsy, vestibular neuronitis, Guillain-Barre syndrome, neuromyelitis optica, vertigo, seizures, neurofibromatosis type 1, mitochondria disease (POLG mutation), mylopathy, Parkinson's disease, Parkinson's disease/MS, stroke, central retinal artery occlusion, neuromyelitis optic, neuromyelitis optic/MS, diabetes type 2/MS, unknown/toxic optic neuropathy, migraines, facial spasms, Horner's syndrome, chronic inflammatory demyelinating neuropathy, diplopia, Meniere's disease, rheumatoid arthritis, and epilepsy.

Figure 5:
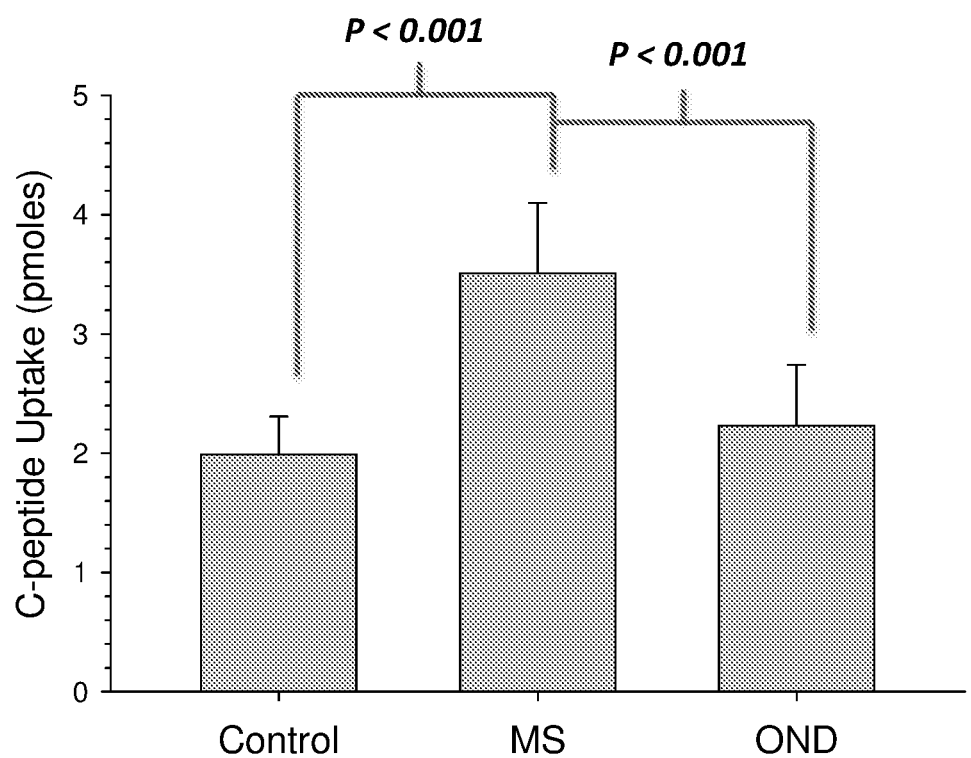
FIG. 5 is a bar graph showing C-peptide binding to blood from control patients, patients with MS, and patients with a non-MS neurological disease (OND).

All samples were handled in an identical manner. Briefly, about 10 mL of blood was drawn from each donor; the RBCs were purified by centrifugation; and the RBCs were suspended in physiological salt solution (PSS). Then RBCs were combined with PSS (containing bovine serum albumin (BSA) as a C-peptide binding facilitator) and C-peptide to generate a mixture having a 7% hematocrit, 20 nM C-peptide, and 75 µM BSA (0.5%). The mixture was allowed to incubate for 2 hours at 37° C. Next, the samples were centrifuged to separate the cells from solution, the solution was diluted 1:50 with double distilled water, and the amount of C-peptide remaining in the solution was determined by ELISA. This provided a value corresponding to the moles of C-peptide bound to the RBCs. FIG. 5 shows the average amount of C-peptide bound to the RBCs obtained from patients with MS, OND, and healthy controls. Whereas blood from the healthy controls bound an average of 1.99±0.32 pmoles C-peptide, blood from MS patients and OND patients bound averages of 3.51±0.59 pmoles of C-peptide and 2.23±0.51 pmoles of C-peptide, respectively. As shown by p values of less than 0.001, the increase in C-peptide binding relative to healthy controls and OND patients is significant.

Figure 6:
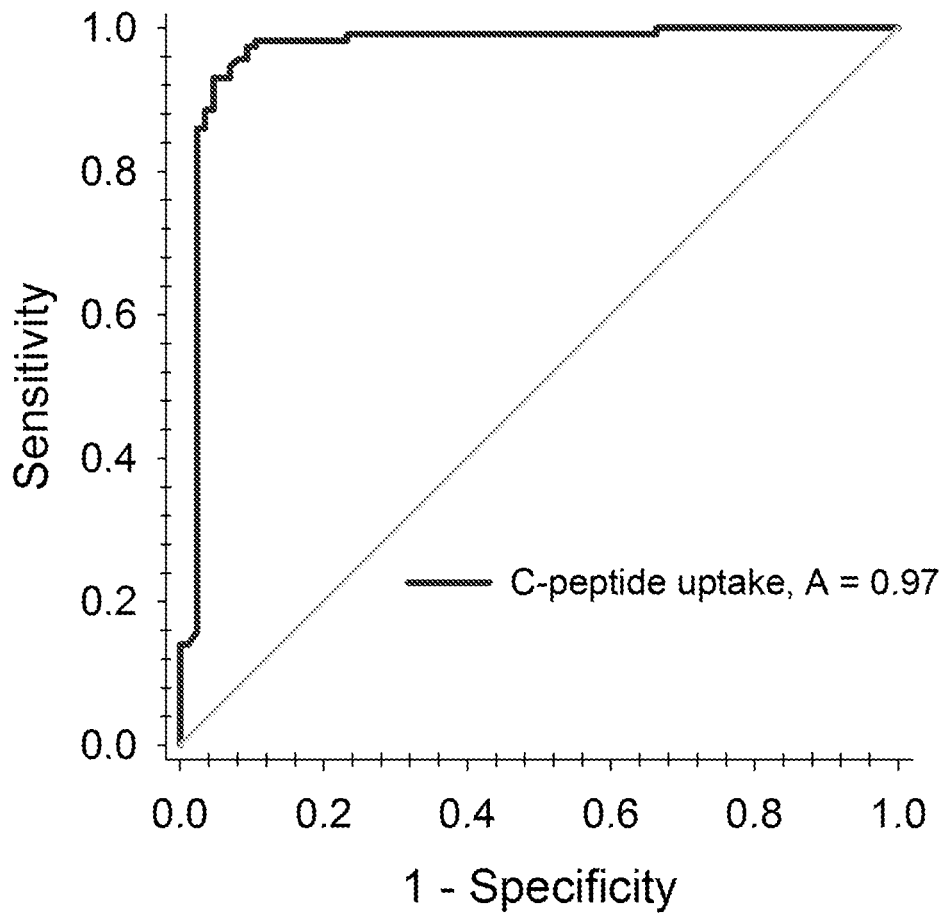
FIG. 6 is receiver operating characteristic (ROC) curve generated by performing a method according to the current technology.

A Receiver Operating Characteristic (ROC) Curve was generated to demonstrate the tradeoff between sensitivity and specificity, where any increase in sensitivity is accompanied by a decrease in specificity. The ROC Curve plots the true positive rate (TPR) against a false positive rate (FPR) for different possible cutpoints (C-peptide binding to RBCs) of a diagnostic test. An area under a curve (AUC) of 1 is representative of a perfect diagnostic and AUCs greater than 0.9 are generally considered excellent. FIG. 6 shows a ROC curve generated for the binding experiment including 200 patients; 86 MS patients, and 114 controls (39 patients without MS or OND and 75 patients with OND). The area under the curve is 0.97, which confirms that the diagnostic test is excellent. Moreover, when the healthy controls were not considered, the resulting ROC curve still demonstrated an excellent AUC of 0.96 (data not shown).

Figure 7:
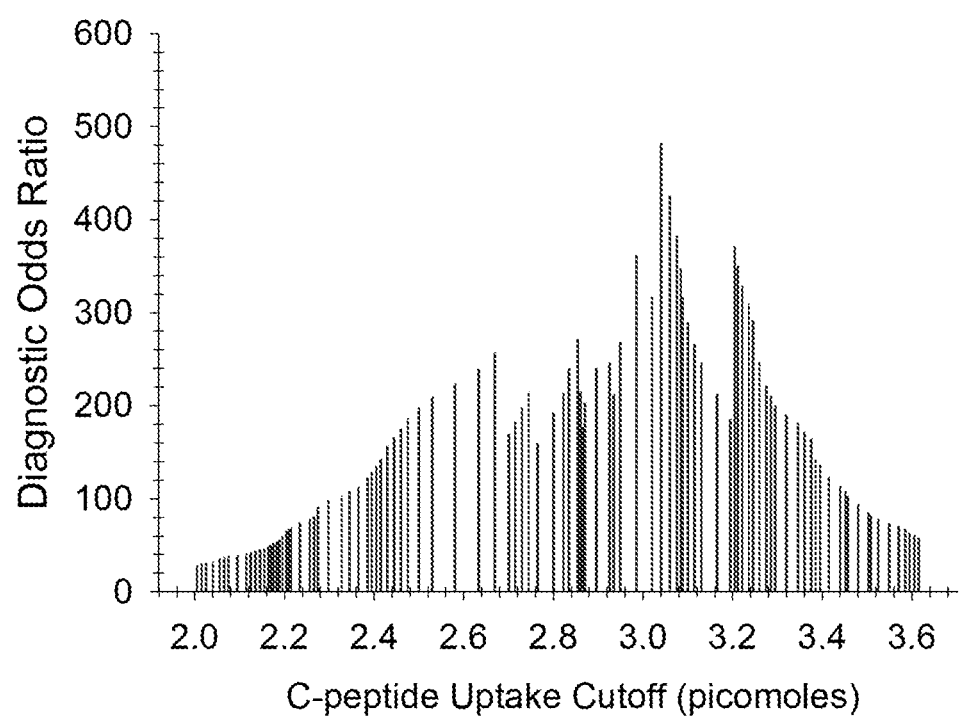
FIG. 7 is a diagnostic odds ratio (DOR) plot showing the sensitivity and specificity of a method according to the current technology.

To further demonstrate the sensitivity and specificity of the binding experiment, a diagnostic odds ratio (DOR) was determined. The DOR compares the odds of positivity in diseased relative to the odds of positivity in the non-diseased. DOR values range from 0 to infinity, with higher values indicating better discriminatory test performance. With the same sensitivity to the test, DOR increases with an increase of a test specificity. FIG. 7 shows a DOR plot generated for the binding experiment including the 200 patients. The plot shows a DOR of greater than 315 across cutpoints between 2.99 and 3.08 pmoles of C-peptide binding. The plot shows a maximum DOR of 481 at 3.04 pmoles of C-peptide binding. Therefore, the DOR further demonstrates excellent sensitivity and specificity of the binding experiment. When healthy controls are not included in the control data set, the DOR was determined to be greater than 200 across cutpoints between 2.99 and 3.08 picomoles of C-peptide binding with a maximum DOR of 312 at 3.04 picomoles of C-peptide binding (data not shown).

Example 3

Experiments were performed to determine the effect of hematocrit on C-peptide binding to RBCs. The experiment was conducted as described above in Experiment 2, except various hematocrits were tested. The results are provided in Table 1. Table 1 shows that there is less C-peptide binding to RBCs when a lower hematocrit is used. Conversely, the table shows that there is greater C-peptide binding to RBCs when a higher hematocrit is used. In general, increase the hematocrit results in a substantially linear increase in C-peptide binding when the RBCs are saturated with C-peptide.

TABLE 1

Effect of hematocrit on
C-peptide binding by RBCs

| Hematocrit | Control (pmoles) | MS (pmoles) |
|---|---|---|
| 3.50% | 1.18 | 1.63 |
| 7% | 2.18 | 3.38 |
| 14% | 4.78 | 6.25 |

Example 4

Experiments were performed to determine the stability of the whole blood. The experiment was conducted as described above in Experiment 2, except the blood was stored in citrate tubes at 4° C. over a period of 4 days during the experiment. Only blood from healthy patients was tested. The results are provided in Table 2. Table 2 shows that C-peptide binding slightly decreases from day-to-day over the 4-day period.

TABLE 2

Effect of storing blood on
C-peptide binding by RBCs

| Day | C-peptide binding (pmoles) |
|---|---|
| 1 | 2.38 |
| 2 | 2.23 |
| 3 | 2.14 |
| 4 | 1.83 |

Example 5

Experiments were performed to determine the stability of supernatant generated after separating cells from solution as described in Experiment 2. The protocol of Experiment 2 was repeated on blood from healthy patients, but the supernatant was stored at 4° C. for from 1 to 3 days prior to determining C-peptide binding by the RBCs. The results are provided in Table 3. Table 3 shows that storing the supernatant at 4° C. for from 1 to 3 days has little effect on the amount of C-peptide determined to be in the supernatant.

TABLE 3

Effect of short-term storage of supernatant
on C-peptide binding calculations

| Day | C-peptide binding (pmoles) |
|---|---|
| 1 | 2.23 |
| 2 | 2.17 |
| 3 | 2.20 |

Example 6

Experiments were performed to determine the stability of supernatant generated after separating cells from solution as described in Experiment 2. The protocol of Experiment 2 was repeated on blood from healthy patients, but the supernatant was stored at −20° C. from 0 (day of draw) to 6 weeks prior to determining C-peptide binding by the RBCs. The results are provided in Table 4. Table 4 shows that freezing the supernatant for from 0 to 6 weeks resulted in only a slight decrease in C-peptide binding over the 6 week period.

TABLE 4

Effect of long-term storage of supernatant on
C-peptide binding calculations

| Week | C-peptide binding (pmoles) |
|---|---|
| 0 | 2.45 |
| 1 | 2.48 |
| 3 | 2.30 |
| 6 | 2.34 |

Example 7

Experiments were performed to determine the effect of C-peptide binding facilitator concentration on C-peptide binding by RBCs. The protocol of Experiment 2 was repeated, but with increasing BSA concentrations. The results are shown in Table 5. Table 5 shows that increasing the BSA concentration from 0.5% to 2.0% has little effect on C-peptide binding. Only a slight increase in C-peptide binding is realized.

TABLE 5

Effect of BSA concentration of C-peptide binding to RBCs

| [BSA] | C-peptide binding (pmoles) |
|---|---|
| 0.5% | 2.14 ± 0.22 |
| 1.0% | 2.19 ± 0.16 |
| 2.0% | 2.26 ± 0.13 |

Example 8

Experiments were performed to test various potential C-peptide binding facilitators. The experiments were performed as described in example 2, but the C-peptide binding facilitator, BSA, was replaced with other albumins (porcine serum albumin and ovalbumin) or other proteins (leptin, casein, transferrin, and collagen). The results are shown in Tables 6 and 7.

TABLE 6

Effect of other albumins on C-peptide binding to RBCs

| Albumin | Control (pmoles; n = 4) | MS (pmoles; n = 1) |
|---|---|---|
| porcine serum albumin | 4.01 ± 1.01 | 6.33 |
| ovalbumin | 0.39 ± 0.22 | 0.67 |

TABLE 7

Effect of other proteins on C-peptide binding to RBCs

| Protein | Control (pmoles; n = 3) | MS (pmoles; n = 1) |
|---|---|---|
| leptin | 0.74 ± 0.11 | 0.97 |
| casein | No binding detected | No binding detected |
| transferrin | No binding detected | No binding detected |
| collagen | 0.21 ± 0.14 | 0.56 |

Example 9

Experiments were performed to determine if RBCs from MS patients (n=19) release more ATP than blood from healthy control patients (n=10) or blood from MS patents combined with the ATP release inhibitor, glybenclamide (Gly; n=12) when subjected to a constricted environment. RBCs from the patients were washed in PSS and suspended to a 7% hematocrit. A dual syringe pump provided two syringes; a first syringe containing a blood sample and a second syringe containing a detection facilitator (a luciferin/ luciferase mixture). Collectively the blood sample and detection facilitator are referred to as "the solutions." The solutions were individually pumped at 6.7 µL/min through 50 µm internal diameter microbore tubes having a polyimide coating. The solutions met at a mixing T-junction, where they were combined and pumped collectively through 75 µm internal diameter microbore tubing having a portion of the polyimide coating removed. A constricted environment was provided as the solutions combined because the total volume was doubling, but the inner diameter of the tubing was increased by only 50%. As the RBCs are deformed in the constricted environment, they released ATP. The portion of tubing having the polyimide coating removed was positioned over a light-excluding box containing a photomultiplier tube (PMT), such that chemiluminescence generated from the ATP contacting the detection facilitator was detected. The concentrations of ATP were compared to a standard curve prepared by pumping standard concentrations of ATP (instead of blood samples) and detection facilitator (a luciferin/luciferase mixture) through the tubing and over the PMT in the same manner. The cells combined with Gly act as a control to demonstrate that ATP was not released due to cell lysis. The results are shown in FIG. 3. Whereas the blood from the healthy control patients released 132.1±14.1 nM ATP, the blood from the MS patients released 344.7±46.8 nM of ATP; a significantly higher amount (over 2.5 fold higher). However, when blood from MS patients was combined with Gly, the amount of ATP release dropped to 65.3±11.6 nM, which is lower than the blood from the healthy control. Therefore, measuring ATP release from blood can be used to indicate a high probably of having MS.

Example 10

Additional experiments were performed to determine whether a C-peptide facilitator can facilitate binding of C-peptide to cells expressing Glut1 other than RBCs. Endothelial cells (bovine pulmonary artery endothelial cells) were grown to confluency on 12-well tissue culture plates. When the cell reached confluency, they were incubated in Dulbecco's Modified Eagle Medium (DMEM) containing serum for 24 hours. Following incubation, the cells were washed and incubated for 1 hour at 37° C. in the presence of 10 nM $Zn^{2+}$ and C-peptide in DMEM containing serum. The endothelial cells were determined to have bound 2.0±0.1 attomoles of C-peptide per endothelial cell.

Neutrophils from healthy control patients were also tested. The neutrophils were isolated using techniques known in the art. Briefly, blood was drawn into a heparin-coated vacutainer. An equal volume of 3% Dextran was added to drawn whole blood in sterile 50 mL tubes. After inverting, the tubes were set upright for 30 minutes at room temperature to generate a plurality of layers. The top layer was aspirated and transferred to a new 50 mL tube and centrifuged at 500 g for 10 minutes at 4° C. The resulting top layer was discarded. The resulting pellet was resuspended in 10 mL 0.9% saline. After pooling suspensions together in a single tube, it was underplayed with 10 mL of hypaqu-ficoll and centrifuged at 800 g for 15 minutes at room temperature. The resulting liquid band was removed and the remainder was resuspended in 20 mL 0.2% saline and mixed. 20 mL of 1.6% saline was then added to the suspension and it was centrifuged at 250 g for 6 minutes at 4° C. The supernatant was removed and the pellet was suspended in PBS for use in experiments. The cells were counted and then incubated with 20 nM C-peptide for 1 hour at 37° C. to generate an incubated sample. The incubated sample was centrifuged and the amount of C-peptide in the supernatant was determined by ELISA. The neutrophils were determined to have bound 2.68 attomoles of C-peptide per neutrophil.

Example 11

Experiments were performed to determine the relative expression level of Glut1 in RBCs from healthy controls (n=44), MS patients (n=66), and patients with OND (n=57).

RBCs were isolated from the controls and patients as described above. The cells were lysed with a lysis buffer and centrifuged at 23,000×g for 15 minutes at 4° C. A resulting supernatant was discarded and the pellet was subjected to a lysis buffer and then centrifuged again at 23,000×g for 15 minutes at 4° C. A resulting supernatant was discarded and the remaining pellet included cell lysates. Equal amounts of each lysate were subjected to sodium dodecyl sulfate polyacrylamide gel electrophoresis (SDS-PAGE). Western blots were then prepared using anti-Glut1 primary antibodies. Bands corresponding to Glut1 in RBC lysate from the healthy controls, MS patients, and OND patients were scanned and quantified (normalized to the control).

Figure 8:
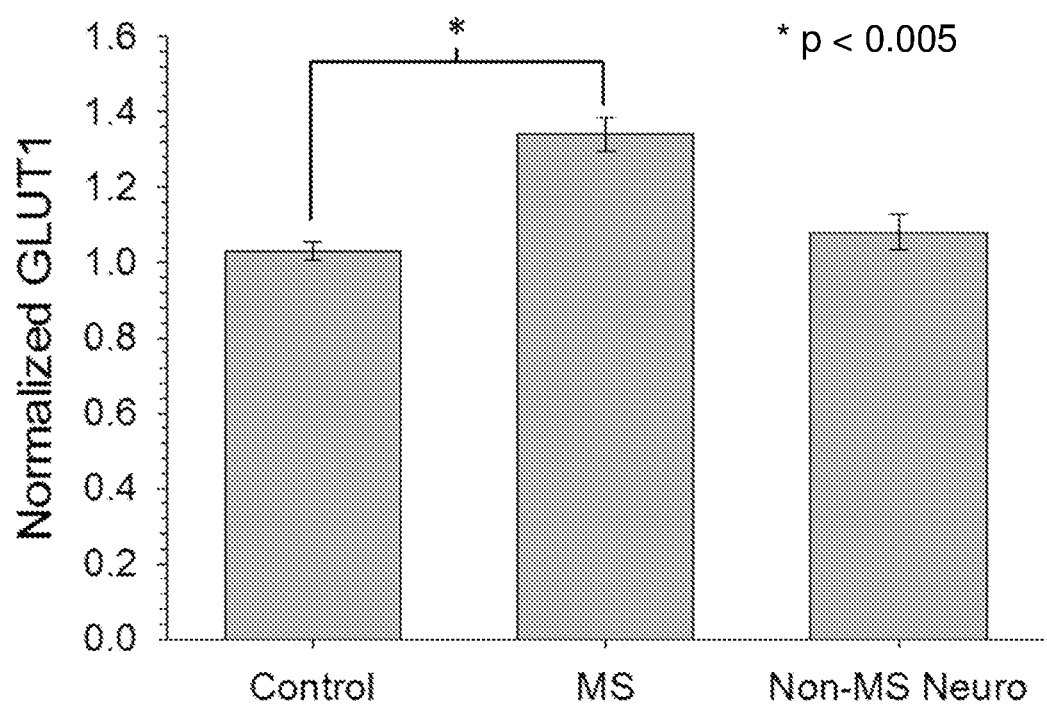
FIG. 8 is a bar graph showing relative amounts of the glucose 1 transporter protein (Glut1) in lysates from healthy control patients, lysates from MS patients, and lysates from patients with a non-MS neurological disease (OND).

The results of the experiment are shown in FIG. 8. FIG. 8 is a graph showing the control as having 1.03±0.026 normalize Glut1, MS as having 1.34±0.045 normalized Glut1, and OND (Non-MS Neuro) as having 1.08±0.047. Whereas the OND lysates contained substantially the same amount of Glut1 as the control lysates, the MS lysates contained about 1.3 fold more Glut1 relative to the control lysates ($p<0.005$).

Example 12

Experiments were performed to determine how much glucose RBCs from MS patients (n=22) bind relative to RBCs from healthy controls (n=11). 7% solutions of purified RBCs from healthy control and MS patients were incubated with $^{14}C$-glucose alone or with $^{14}C$-glucose with 20 nM $Zn^{2+}$ and C-peptide. The solutions were incubated for 4 hours at 37° C. and then centrifuged at 500 g for 4 minutes. A resulting supernatant was discarded and the cells were resuspended in physiological salt solution (PSS). Centrifuging and washing with PSS was repeated twice. The RBCs were then lysed with bleach and incubated for 30 min. to generate lysates. 200 µL of lysate was combined with scintillation cocktail and read, along with standards, on a liquid scintillation counter. Values were normalized to lysates form the healthy control without $Zn^{2+}$ and C-peptide.

Figure 9:
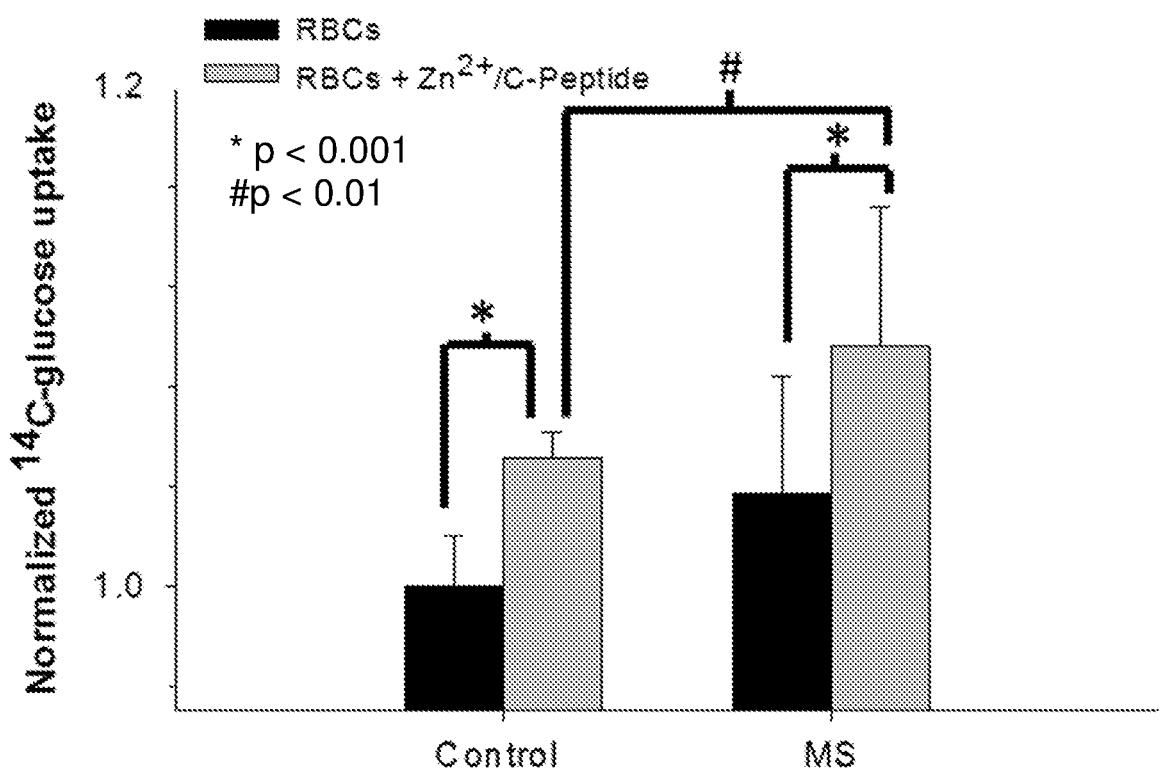
FIG. 9 is a bar graph showing relative amount of glucose associated with healthy control cells and cells form MS patients; with and without $Zn^{2+}$ and C-peptide.

The results of the experiment are shown in FIG. 9. FIG. 9 is a graph showing that, in both RBCs form healthy controls and MS patients, the addition of Zn2+ and C-peptide greatly increases glucose uptake relative to RBCs not contacted with Zn2+ and C-peptide. Moreover, the graph shows that RBCs from MS patients uptake significantly more glucose relative to corresponding controls, with or without $Zn^{2+}$ and C-peptide.

SEQUENCE LISTING

Various amino acid sequences are described herein with sequence identifiers (e.g., SEQ ID NO:_) that correspond to sequences in a sequence listing. The sequence listing constitutes a part of this disclosure.

RECITATION OF EXEMPLARY EMBODIMENTS

The following is a recitation of embodiments exemplifying the materials, methods, kits and reagents of the present technology.
1. A method for measuring C-peptide binding by cells, the method comprising:
  incubating the cells with C-peptide mixture comprising an amount, e.g., known amount, of C-peptide and a C-peptide binding facilitator to produce incubated cells in an incubated cellular mixture; and
  determining the amount of C-peptide bound to the incubated cells.
2. The method according to Embodiment 1, wherein the C-peptide binding facilitator is selected from the group consisting of albumins, leptin, collagen, and mixtures thereof.
3. The method according to Embodiment 2, wherein the C-peptide binding facilitator is an albumin.
4. The method according to Embodiment 3, wherein the albumin is obtained from whole blood or a blood fraction obtained from a human, cow, chicken or pig blood.
5. The method according to Embodiment 3, wherein the albumin is recombinant albumin.
6. The method according to any one of the preceding Embodiments, wherein the C-peptide is a polypeptide comprising the amino acid sequence EGSLQ (SEQ ID NO:17).
7. The method according to Embodiment 6, wherein the C-peptide is a mammalian C-peptide, preferably human C-peptide.
8. The method according to any one of Embodiments 1-5, wherein the C-peptide is selected from the group consisting of a full length wild type C-peptide, a C-peptide molecule having an amino acid sequence at least 75% identical to the amino acid sequence of wild type C-peptide, fractions thereof comprising at least 5 amino acids, and combinations thereof, wherein the C-peptide has the ability to bind to cells in the presence of the C-peptide binding facilitator.
9. The method according to Embodiment 8, wherein the C-peptide is a fraction thereof comprising the five terminal amino acids of a wild type C-peptide, optionally consisting of the amino acid sequence EGSLQ (SEQ ID NO:17).
10. The method according to Embodiment 8, wherein the C-peptide has an amino acid sequence at least 75% identical to the amino acid sequence of a full length C-peptide.
11. The method according to Embodiment 10, wherein the full length C-peptide is isolated from a human, pig, cow, chicken, or zebrafish.
12. The method according to Embodiment 6, wherein the C-peptide is recombinant C-peptide or C-peptide synthesized in vitro.
13. The method according to any one of the preceding Embodiments, wherein the C-peptide is modified with a heterologous moiety.
14. The method according to Embodiment 13, wherein the heterologous moiety is a radioactive label, an enzymatic label, a fluorescent label, a heavy metal label, a fluorescent label, a luminescent label, or an affinity tag.
15. The method according to any one of the preceding Embodiments, wherein the C-peptide binding facilitator comprises a tag for quantifying the C-peptide, preferably wherein the tag comprises FLAG, polyhistidine, hemagglutinin, glutathione-S-transferase, or maltose-binding protein.
16. The method according to any one of the preceding Embodiments, wherein the cells express glucose 1 transporter protein (Glut1).
17. The method according to Embodiment 16, wherein the cells are red blood cells (RBCs), macrophages, neutrophils, or endothelial cells.
18. The method according to any one of the preceding Embodiments, wherein the incubating is performed for from about 1 minute to about 24 hours at a temperature of from about 5° C. to about 50° C.

19. The method according to any one of the preceding Embodiments, wherein the determining an amount of C-peptide bound to the incubated cells comprises:
   separating the incubated cells from the incubated cellular mixture, forming an incubated cell fraction and a supernatant; and
   measuring
     (i) the amount of C-peptide in the incubated cellular fraction; or
     (ii) the amount of C-peptide in the supernatant; or
     (iii) the amount of C-peptide in the supernatant, and subtracting the amount of C-peptide in the supernatant from the known amount of C-peptide; or
     (iv) any combination of (i), (ii), and (iii).

20. The method according to Embodiment 19, wherein the measuring comprises directly detecting C-peptide by detecting a signal provided by a tag coupled to the C-peptide or indirectly detecting C-peptide by detecting an antibody or antibody fraction that binds to the C-peptide.

21. The method according to any one of the preceding Embodiments, wherein the incubating comprises admixing (i) from about 0.05 mL to about 20 mL of a suspension of the cells, (ii) about 1 to about 500 pmoles of the C-peptide, and (iii) the c-peptide binding facilitator to a final concentration of from about 0.05% (w/v) to about 25% (w/v).

22. The method according to Embodiment 21, wherein the suspension of the cells comprises RBCs and has a hematocrit of from about 2% to about 20%.

23. The method according to Embodiment 20, wherein the suspension of the cells is whole blood, or a blood fraction comprising RBCs, membranes of RBCs, neutrophils, macrophages, or leukocytes.

24. The method according to any one of Embodiments 21-23, wherein the C-peptide and c-peptide binding facilitator are components of an isotonic solution.

25. The method according to Embodiment 24, wherein the concentration of C-peptide in the isotonic solution is from about 100 pM to about 1 mM and the concentration of the C-peptide binding facilitator is from about 0.05% (w/v) to about 25% (w/v).

26. The method according to Embodiment 24 or Embodiment 25, wherein the solution comprises a buffer selected from the group consisting of phosphate buffered saline, physiological saline solution, Tris buffer, and phosphate buffer.

27. The method according to any one of Embodiments 24-26, wherein the isotonic solution is admixed with the suspension of the cells.

28. A method of assessing the metabolic activity of cells, comprising performing a method according to any of the preceding Embodiments.

29. A method of detecting a metabolic disorder in a cell, comprising performing a method according to any one of Embodiments 1-27.

30. The method according to Embodiment 29, wherein a determination of the amount of C-peptide bound to the cells of greater than or equal to about 2000 C-peptide molecules per cell is indicative of the metabolic disorder.

31. A method for diagnosing a disorder in a mammalian subject, comprising obtaining cells from the subject and performing a method according to any one of Embodiments 1-27.

32. A method for analyzing the risk of developing a disorder in a mammalian subject, comprising obtaining cells from the subject and performing a method according to any one of Embodiments 1-27.

33. A method for determining the likelihood that a mammalian subject has a disorder, comprising obtaining cells from the subject and performing a method according to any one of Embodiments 1-27.

34. The method according to any one of Embodiment 31-33, wherein the disorder is an immune-mediated disease.

35. The method according to Embodiment 34, wherein the disorder is multiple sclerosis (MS).

36. A method for diagnosing a disorder in a mammalian subject, comprising effecting a method for measuring C-peptide in cells obtained from the subject, the method comprising a method according to any one of Embodiments 1-27.

37. A method for analyzing the risk of developing a disorder in a mammalian subject, comprising effecting a method for measuring C-peptide binding in cells obtained from the subject, the assay comprising a method according to any one of Embodiments 1-27.

38. A method for determining the likelihood that a mammalian subject has a disorder, comprising effecting an assay for measuring C-peptide in cells obtained from the subject, the assay comprising a method according to any one of Embodiments 1-27.

39. The method according to any one of Embodiments 36-38, wherein the disorder is an immune-mediated disease.

40. The method according to Embodiment 35, wherein the disorder is MS.

41. An in vitro method for assessing the probability that a mammalian subject has an immune-mediated disease, the method comprising:
   incubating cells that express glucose 1 transporter protein (Glut1) obtained from the subject with a C-peptide composition comprising an amount, e.g., known amount, of C-peptide and an albumin under conditions that allow for the cells to bind the C-peptide to form incubated cells in an incubated cellular mixture;
   separating the incubated cells from the incubated cellular mixture; and
   determining the amount of C-peptide bound to the incubated cells.

42. The method according to Embodiment 41, further comprising comparing the amount of C-peptide bound to the incubated cells to a reference amount determined by performing the incubating, separating and determining using cells obtained from a second subject that does not have the immune-mediated disease.

43. The method according to Embodiment 42, wherein an amount of C-peptide bound to the incubated cells greater than or equal to about 1.5 fold relative to the reference amount is indicative of a high probability of the subject having the immune-mediated disease.

44. The method according to Embodiment 41, wherein a level of C-peptide bound to the incubated cells of greater than or equal to about 2000 molecules/cell is indicative of the immune-mediated disease in the subject.

45. The method according to Embodiment 41, wherein the albumin is obtained from whole blood or a blood fraction obtained from human, cow, chicken or pig blood.

46. The method according to Embodiment 45, wherein the albumin is recombinant albumin.

47. The method according to any one of Embodiments 41-46, wherein the C-peptide is a polypeptide comprising the amino acid sequence EGSLQ (SEQ ID NO:17).

48. The method according to Embodiment 47, wherein the C-peptide is a mammalian C-peptide, preferably human C-peptide.

49. The method according to any one of Embodiments 41-46, wherein the C-peptide is selected from the group consisting of a full length wild type C-peptide, a C-peptide molecule having an amino acid sequence at least 75% identical to the amino acid sequence of wild type C-peptide, fractions thereof comprising at least 5 amino acids, and combinations thereof, wherein the C-peptide has the ability to bind to cells in the presence of the C-peptide binding facilitator.

50. The method according to Embodiment 49, wherein the C-peptide is a fraction thereof comprising the five terminal amino acids of a wild type C-peptide, optionally consisting of the amino acid sequence EGSLQ 51. The method according to Embodiment 49, wherein the C-peptide has an amino acid sequence at least 75% identical to the amino acid sequence of a full length C-peptide.

52. The method according to Embodiment 51, wherein the full length C-peptide is isolated from a human, pig, cow, chicken, or zebrafish.

53. The method according to Embodiment 47, wherein the C-peptide is recombinant C-peptide or C-peptide synthesized in vitro.

54. The method according to any one of Embodiments 41-53, wherein the C-peptide is modified with a heterologous moiety.

55. The method according to Embodiment 54, wherein the heterologous moiety is a radioactive label, an enzymatic label, a fluorescent label, a heavy metal label, a fluorescent label, a luminescent label, or an affinity tag.

56. The method according to any one of Embodiments 41-55, wherein the C-peptide binding facilitator comprises a tag for quantifying the C-peptide, preferably wherein the tag comprises FLAG, polyhistidine, hemagglutinin, glutathione-S-transferase, or maltose-binding protein.

57. The method according to any one of Embodiments 41-56, wherein the cells express Glut1.

58. The method according to Embodiment 57, wherein the cells are red blood cells (RBCs), macrophages, neutrophils, or endothelial cells.

59. The method according to any one of the preceding Embodiments, wherein the incubating is performed for from about 1 minute to about 24 hours at a temperature of from about 5° C. to about 50° C.

60. The method according to any one of Embodiments 41-59, wherein the determining an amount of C-peptide bound to the incubated cells comprises:
  separating the incubated cells from the incubated cellular mixture, forming an incubated cell fraction and a supernatant; and
  measuring
  (i) the amount of C-peptide in the incubated cellular fraction; or
  (ii) the amount of C-peptide in the supernatant; or
  (iii) the amount of C-peptide in the supernatant, and subtracting the amount of C-peptide in the supernatant from the known amount of C-peptide; or
  (iv) any combination of (i), (ii), and (iii).

61. The method according to Embodiment 60, wherein the measuring comprises directly detecting C-peptide by detecting a signal provided by a tag coupled to the C-peptide or indirectly detecting C-peptide by detecting an antibody or antibody fraction that binds to the C-peptide.

62. The method according to any one of Embodiments 41-61, wherein the incubating comprises admixing (i) from about 0.05 mL to about 20 mL of a suspension of the cells, (ii) about 1 to about 500 pmoles of C-peptide, and (iii) C-peptide binding facilitator to a final concentration of from about 0.05% (w/v) to about 25% (w/v).

63. The method according to Embodiment 62, wherein the suspension of the cells comprises RBCs and has a hematocrit of from about 2% to about 20%.

64. The method according to Embodiment 61, wherein the suspension of the cells is whole blood, or a blood fraction comprising RBCs, membranes of RBCs, neutrophils, macrophages, or leukocytes.

65. The method according to any one of Embodiments 62-64, wherein the C-peptide and C-peptide binding facilitator are components of an isotonic solution.

66. The method according to Embodiment 65, wherein the concentration of C-peptide in the isotonic solution is from about 100 pM to about 1 mM and the concentration of the C-peptide binding facilitator is from about 0.05% (w/v) to about 25% (w/v).

67. The method according to any one of Embodiments 41-66, wherein the immune-mediated disease is MS.

68. A method of analyzing the risk of an immune-mediated disease in a mammalian subject, comprising effecting an assay on cells obtained from the subject, the assay comprising a method according to any one of Embodiments 41-67.

69. A kit for use measuring C-peptide binding by cells, the kit comprising a C-peptide binding facilitator, C-peptide, and a container.

70. A kit according to Embodiment 69, wherein the container is operable for mixing a solvent with one or both of the C-peptide binding facilitator and the C-peptide.

71. A kit according to Embodiment 70, wherein the container is operable for mixing one or both of the C-peptide binding facilitator and the C-peptide with a suspension of the cells.

72. A kit according to Embodiment 69, wherein the container is a first container containing the C-peptide binding facilitator, and the kit further comprises a second container containing C-peptide.

73. The kit according to any one of Embodiments 69-72, wherein the C-peptide binding facilitator is an albumin.

74. The kit according to Embodiment 73, wherein the albumin is in powdered form, preferably wherein the albumin is lyophilized.

75. The kit according to any one of Embodiments 69-74, wherein the C-peptide is in powdered form, preferably wherein the C-peptide is lyophilized.

76. The kit according to Embodiment 72, further comprising a third container containing a solvent for one or both of the C-peptide binding facilitator and the C-peptide.

77. The kit according to Embodiment 76, wherein the solvent comprises phosphate buffered saline, physiological saline solution, Tris buffer, or phosphate buffer.

78. The kit according to Embodiment 76 or Embodiment 77, further comprising a fourth container operable for receiving the cells.

79. The kit according to any one of Embodiments 69-78, further comprising a reagent for determining an amount of C-peptide bounded by the cells.

80. A method for measuring C-peptide binding by cells using the kit according to any one of Embodiments 69-79.

81. The method according to Embodiment 80, the method comprising:
  mixing the C-peptide binding facilitator and the C-peptide to form a C-peptide/facilitator mixture;
  incubating the cells with the C-peptide/facilitator mixture to produce incubated cells in an incubated cellular mixture; and determining the amount of C-peptide bound to the incubated cells.

82. A method for measuring C-peptide binding by cells using the kit according to Embodiment 76 or Embodiment 77, the method comprising:
mixing the C-peptide binding facilitator and the C-peptide to form a C-peptide/facilitator mixture;
incubating the cells with the C-peptide/facilitator mixture to produce incubated cells in an incubated cellular mixture; and
determining the amount of C-peptide bound to the incubated cells.

83. The method according to Embodiment 82, wherein C-peptide/facilitator mixture is an isotonic solution comprising the C-peptide and C-peptide binding facilitator.

84. The method according to Embodiment 82, wherein the isotonic solution comprises the solvent in the third container.

85. The method according to Embodiment 81, wherein the mixing and contacting are performed simultaneously or sequentially in the first container or second container.

86. The method according to Embodiment 82, wherein the mixing and contacting are performed simultaneously or sequentially in the third container.

87. The method according to Embodiment 82, wherein the kit comprises a fourth container and the mixing and contacting are performed simultaneously or sequentially in the fourth container.

88. The method according to Embodiment 82 comprising transferring a predetermined volume of the solvent in the third container to one of the first container or the second container and dissolving the contents of the first container or the second container in the solution to form a first working solution;
transferring the partial working solution to the other of the first container or the second container and dissolving the contents of the other of the first container or the second container to form a second working solution;
incubating a suspension of the cells with the second working solution to generate a C-peptide cellular mixture under conditions that allow for the cells to bind the C-peptide.

89. The method according to Embodiment 88, further comprising:
contacting a detection reagent with the second working solution; and
measuring the amount of C-peptide in the second working solution.

90. The method according to any one of Embodiments 81-89, wherein the incubating comprises admixing (i) from about 0.05 mL to about 20 mL of a suspension of the cells, (ii) about 1 to about 500 pmoles of the C-peptide, and (iii) the C-peptide binding facilitator to a final concentration of from about 0.05% (w/v) to about 25% (w/v).

91. The method according to Embodiment 90, wherein the suspension of the cells comprises red blood cells (RBCs) and has a hematocrit of from about 2% to about 20%.

92. The method according to Embodiment 90, wherein the suspension of the cells is whole blood, or a blood fraction comprising RBCs, membranes of RBCs, neutrophils, macrophages, or leukocytes.

93. The method according to any one of Embodiments 81-92, wherein the concentration of C-peptide is from about 100 pM to about 1 mM and the concentration of the C-peptide binding facilitator is from about 0.05% (w/v) to about 25% (w/v).

94. A reagent for use in measuring C-peptide binding to cells that express glucose 1 transporter protein (Glut1), the reagent consisting essentially of albumin dissolved in an isotonic solution and, optionally, further consisting of an optional component selected from the group consisting of C-peptide, a buffering agent, $Zn^{2+}$, $Fe^{2+}$, $Cr^{3+}$, and mixtures thereof.

95. The reagent according to Embodiment 94, wherein the buffering agent is selected from the group consisting of phosphate salts, tris(hydroxymethyl)aminomethane, and mixtures thereof.

96. The reagent according to Embodiment 94, containing C-peptide.

97. A method for measuring C-peptide binding by cells using the reagent of any of Embodiments 94-96.

98. A method for detecting a metabolic disorder in a cell using the reagent of any of Embodiments 94-96.

99. The method according to Embodiment 97 or Embodiment 98, comprising incubating from about 0.05 mL to about 5 mL of a the suspension of the cells with the reagent, wherein the reagent comprises from about 1 to about 50 pmoles of the C-peptide, and a C-peptide binding facilitator to a final concentration of from about 0.05% (w/v) to about 10% (w/v).

100. The method according to Embodiment 99, wherein the suspension of the cells comprises red blood cells (RBCs) and has a hematocrit of from about 2% to about 20%.

101. The method according to Embodiment 100, wherein the suspension of the cells is whole blood, or a blood fraction comprising RBCs, membranes of RBCs, neutrophils, macrophages, or leukocytes.

102. The method according to any one of Embodiments 97-101, wherein the concentration of C-peptide in the reagent is from about 100 pM to about e and the concentration of the C-peptide binding facilitator in the reagent is from about 0.05% (w/v) to about 10% (w/v).

103. A reagent for use in measuring C-peptide binding to cells that express glucose 1 transporter protein (Glut1), the reagent consisting essentially of C-peptide dissolved in an isotonic solution and, optionally, further consisting of an optional component selected from the group consisting of albumin, a buffering agent, Zn, Fe, Cr, and mixtures thereof.

104. The reagent according to Embodiment 103, containing a buffering agent is selected from the group consisting of phosphate salts, tris(hydroxymethyl)aminomethane, and mixtures thereof.

105. The reagent according to Embodiment 103, containing albumin.

106. A method for measuring C-peptide binding to cells using the reagent of any of Embodiments 103-105.

107. A method for detecting a metabolic disorder in a cell using the reagent of any of Embodiments 103-105.

108. The method according to Embodiment 106 or Embodiment 107, comprising contacting from about 0.05 mL to about 20 mL of a suspension of the cells with the reagent, wherein the reagent comprises from about 1 to about 500 pmoles of the C-peptide, and C-peptide binding facilitator to a final concentration of from about 0.05% (w/v) to about 25% (w/v).

109. The method according to Embodiment 108, wherein the suspension of the cells comprises red blood cells (RBCs) and has a hematocrit of from about 2% to about 20%.

110. The method according to Embodiment 109, wherein the suspension of the cells is whole blood, or a blood fraction comprising RBCs, membranes of RBCs, neutrophils, macrophages, or leukocytes.

111. The method according to any one of Embodiments 106-110, wherein the concentration of C-peptide in the reagent is from about 100 pM to about 1 mM and the concentration of the C-peptide binding facilitator in the reagent is from about 0.05% (w/v) to about 25% (w/v).

112. An in vitro method for diagnosing a mammalian subject as having an immune-mediated disease, the method comprising:
   incubating, in the presence of albumin, red blood cells (RBCs) from the subject with C-peptide under conditions that allow for binding of C-peptide by red blood cells; and
   determining the amount of C-peptide bound by the RBCs, wherein increased binding of C-peptide by the RBCs, relative to a control C-peptide binding level, indicates that the subject has the immune-mediated disease.

113. The method according to Embodiment 112, wherein the immune-mediated disease is an inflammatory demyelinating disorder.

114. The method according to Embodiment 113, wherein the inflammatory demyelinating disorder is MS.

115. The method according to Embodiment 112, wherein the albumin is obtained from whole blood or a blood fraction obtained from human, cow, chicken or pig blood.

116. The method according to Embodiment 112, wherein the albumin is recombinant albumin.

117. The method according to any one of Embodiments 112-116, wherein the C-peptide is a polypeptide comprising the amino acid sequence EGSLQ 118. The method according to Embodiment 117, wherein the C-peptide is a mammalian C-peptide, preferably human C-peptide.

119. The method according to Embodiment 112, wherein the C-peptide is selected from the group consisting of a full length wild type C-peptide, a C-peptide molecule having an amino acid sequence at least 75% identical to the amino acid sequence of wild type C-peptide, fractions thereof comprising at least 5 amino acids, and combinations thereof, wherein the C-peptide has the ability to bind to cells in the presence of the albumin.

120. The method according to Embodiment 119, wherein the C-peptide is a fraction thereof comprising the five terminal amino acids of a wild type C-peptide, optionally consisting of the amino acid sequence EGSLQ (SEQ ID NO:17).

121. The method according to Embodiment 119, wherein the C-peptide has an amino acid sequence at least 75% identical to the amino acid sequence of a full length C-peptide.

122. The method according to Embodiment 121, wherein the full length C-peptide is isolated from a human, pig, cow, chicken, or zebrafish.

123. The method according to Embodiment 117, wherein the C-peptide is recombinant C-peptide or C-peptide synthesized in vitro.

124. The method according to any one of Embodiments 112-123, wherein the C-peptide is modified with a heterologous moiety.

125. The method according to Embodiment 124, wherein the heterologous moiety is a radioactive label, an enzymatic label, a fluorescent label, a heavy metal label, a fluorescent label, a luminescent label, or an affinity tag.

126. The method according to any one of Embodiments 112-125, wherein the albumin comprises a tag for quantifying the C-peptide, preferably wherein the tag comprises FLAG, polyhistidine, hemagglutinin, glutathione-S-transferase, or maltose-binding protein.

127. The method according to any one of Embodiments 112-126, wherein the cells express glucose 1 transporter protein (Glut1).

128. The method according to Embodiment 127, wherein the cells are RBCs, macrophages, neutrophils, or endothelial cells.

129. The method according to any one of Embodiments 112-128, wherein the incubating is performed for from about 1 minute to about 24 hours at a temperature of from about 5° C. to about 50° C.

130. The method according to any one of Embodiments 112-129, wherein the determining an amount of C-peptide bound to the incubated cells comprises:
   separating the incubated cells from the incubated cellular mixture, forming an incubated cell fraction and a supernatant; and
   measuring
      (i) the amount of C-peptide in the incubated cellular fraction; or
      (ii) the amount of C-peptide in the supernatant; or
      (iii) the amount of C-peptide in the supernatant, and subtracting the amount of C-peptide in the supernatant from the known amount of C-peptide; or
      (iv) any combination of (i), (ii), and (iii).

131. The method according to Embodiment 130, wherein the measuring comprises directly detecting C-peptide by detecting a signal provided by a tag coupled to the C-peptide or indirectly detecting C-peptide by detecting an antibody or antibody fraction that binds to the C-peptide.

132. The method according to any one of Embodiments 112-131, wherein the incubating comprises admixing (i) from about 0.05 mL to about 20 mL of a suspension of the cells, (ii) about 1 to about 500 pmoles of the C-peptide, and (iii) the C-peptide binding facilitator to a final concentration of from about 0.05% (w/v) to about 25% (w/v).

133. The method according to Embodiment 132, wherein the suspension of the cells comprises RBCs and has a hematocrit of from about 2% to about 20%.

134. The method according to Embodiment 131, wherein the suspension of the cells is whole blood, or a blood fraction comprising RBCs, membranes of RBCs, neutrophils, macrophages, or leukocytes.

135. The method according to any one of Embodiments 132-134, wherein the C-peptide and C-peptide binding facilitator are components of an isotonic solution.

136. The method according to Embodiment 135, wherein the concentration of C-peptide in the isotonic solution is from about 100 pM to about 1 mM and the concentration of the albumin is from about 0.05% (w/v) to about 25% (w/v).

137. A method of managing MS in a subject in need thereof, the method comprising:
   (a) effecting an assay for measuring C-peptide binding on cells obtained from the subject, the assay comprising
      (i) incubating the cells with a C-peptide composition comprising an amount, e.g., known amount, of C-peptide and a C-peptide binding facilitator to produce incubated cells in an incubated cellular mixture; and
      (ii) determining the amount of C-peptide bound to the incubated cells.
   (b) comparing the amount of C-peptide bound by the cells to a reference amount determined by performing the assay on cells obtained from a second subject that does not have the immune-mediated disease;
   (c) administering a first treatment for MS; an
   (d) assessing the efficacy of the administering by repeating the effecting and comparing.

138. The method of Embodiment 137, further comprising administering a second treatment of MS after the assessing, wherein the second treatment is altered from the first treatment based on the results of the assessing.

139. A method of assessing the responsiveness of a mammalian subject having MS to a treatment for the MS, comprising a method according to Embodiment 137.

Non-Limiting Discussion of Terminology

The headings (such as "Introduction" and "Summary") and sub-headings used herein are intended only for general organization of topics within the present technology, and are not intended to limit the present technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition or method.

The description and specific examples, while indicating embodiments of the technology, are intended for purposes of illustration only and are not intended to limit the scope of the technology. Moreover, recitation of multiple embodiments having stated features is not intended to exclude other embodiments having additional features, or other embodiments incorporating different combinations of the stated features. Specific examples are provided for illustrative purposes of how to make and use the compositions and methods of this technology and, unless explicitly stated otherwise, are not intended to be a representation that given embodiments of this technology have, or have not, been made or tested. Equivalent changes, modifications and variations of some embodiments, materials, compositions and methods can be made within the scope of the present technology, with substantially similar results.

As used herein, the words "preferred" or "preferable" or "preferably" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

Although the open-ended term "comprising," as a synonym of non-restrictive terms such as including, containing, or having, is used herein to describe an embodiment of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Unless otherwise defined, all technical and scientific terms used herein have the same meaning as commonly understood by one of ordinary skill in the art to which the present technology pertains. In case of conflict, this disclosure, including definitions, will control.

Throughout this disclosure, the numerical values represent approximate measures or limits to ranges to encompass minor deviations from the given values and embodiments having about the value mentioned as well as those having exactly the value mentioned. All numerical values of parameters (e.g., of quantities or conditions) in this specification, including the appended embodiments, are to be understood as being modified in all instances by the term "about" whether or not "about" actually appears before the numerical value. "About" indicates that the stated numerical value allows some slight imprecision (with some approach to exactness in the value; approximately or reasonably close to the value; nearly). If the imprecision provided by "about" is not otherwise understood in the art with this ordinary meaning, then "about" as used herein indicates at least variations that may arise from ordinary methods of measuring and using such parameters.

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9. As referred to herein, ranges are, unless specified otherwise, inclusive of endpoints and include disclosure of all distinct values and further divided ranges within the entire range. Thus, for example, a range of "from A to B" or "from about A to about B" is inclusive of A and of B.

As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments While the present technology has been described with reference to the specific embodiments thereof, it should be understood by those skilled in the art that various changes may be made and equivalents may be substituted without departing from the true spirit and scope of the technology. In addition, many modifications may be made to adapt a particular situation, material, composition of matter, process, process step or steps, to the objective, spirit and scope of the present technology. All such modifications are intended to be within the scope of the technology.

What is claimed is:

1. A method for assessing the probability that a mammalian subject has multiple sclerosis (MS), the method comprising:
effecting an assay comprising:
incubating red blood cells obtained from the subject with a C-peptide mixture comprising a known or unknown amount of C-peptide and a C-peptide binding facilitator to produce incubated red blood cells in an incubated cellular mixture, wherein the C-peptide binding facilitator is bovine serum albumin, porcine serum albumin, ovalbumin, leptin, collagen, or mixtures thereof; and
determining the amount of C-peptide bound to the incubated red blood cells; and
when the amount of C-peptide bound to the incubated red blood cells is greater than about 10% of a normal control value obtained from at least one subject that does not have MS, effecting an administration of a composition that either reduces the frequency of symptoms associated with MS or delays the onset of symptoms associated with MS.

2. The method according to claim 1, wherein the determining an amount of C-peptide bound to the incubated red blood cells comprises:
separating the incubated red blood cells from the incubated cellular mixture, forming an incubated red blood cell fraction and a supernatant; and
measuring
(i) the amount of C-peptide in the incubated red blood cell fraction; or
(ii) the amount of C-peptide in the supernatant; or
(iii) the amount of C-peptide in the supernatant, and subtracting the amount of C-peptide in the supernatant from the known amount of C-peptide; or
(iv) any combination of (i), (ii), and (iii).

3. The method according to claim 2, wherein the measuring comprises directly detecting C-peptide by detecting a signal provided by a tag coupled to the C-peptide or indirectly detecting C-peptide by detecting an antibody or antibody fraction that binds to the C-peptide.

4. The method according to claim 1, wherein the C-peptide and C-peptide binding facilitator are components of an isotonic solution.

5. An in vitro method for assessing the probability that a mammalian subject has multiple sclerosis (MS), the method comprising:
incubating red blood cells obtained from the subject with a C-peptide composition comprising a known or unknown amount of C-peptide and bovine serum albumin, porcine serum albumin, ovalbumin, or a combination thereof under conditions that allow for the red blood cells to bind the C-peptide to form incubated red blood cells in an incubated cellular mixture;
separating the incubated red blood cells from the incubated cellular mixture; and
determining the amount of C-peptide bound to the incubated red blood cells.

6. The method according to claim 5, further comprising comparing the amount of C-peptide bound to the incubated red blood cells to a reference amount determined by performing the incubating, separating and determining, using red blood cells obtained from a second subject that does not have MS.

7. The method according to claim 6, wherein an amount of C-peptide bound to the incubated red blood cells greater than or equal to about 1.5 fold relative to the reference amount is indicative of a high probability of the subject having MS.

8. The method according to claim 5, wherein the incubating comprises admixing (i) from about 0.05 mL to about 5 mL of a suspension of the red blood cells, (ii) about 1 to about 50 pmoles of C-peptide, and (iii) the bovine serum albumin, porcine serum albumin, ovalbumin, or the combination thereof to a final concentration of from about 0.05% (w/v) to about 10% (w/v).

9. The method according to claim 8, wherein the suspension of the red blood cells has a hematocrit of from about 2% to about 20%.

10. The method according to claim 5, wherein the C-peptide is modified with a heterologous moiety.

11. A method of managing multiple sclerosis (MS) in a subject in need thereof, the method comprising:
(a) effecting an assay for measuring C-peptide binding on red blood cells obtained from the subject, the assay comprising
(i) incubating the red blood cells with a C-peptide composition comprising C-peptide and a C-peptide binding facilitator to produce incubated red blood cells in an incubated cellular mixture, the C-peptide binding facilitator being bovine serum albumin, porcine serum albumin, ovalbumin, leptin, collagen, or mixtures thereof; and
(ii) determining the amount of C-peptide bound to the incubated red blood cells;
(b) comparing the amount of C-peptide bound by the red blood cells to a reference amount determined by performing the assay on red blood cells obtained from a second subject that does not have MS;
(c) administering a first treatment for MS; and
(d) assessing the efficacy of the administering by repeating the effecting and comparing.

12. The method of claim 11, further comprising administering a second treatment of MS after the assessing, wherein the second treatment is altered from the first treatment based on the results of the assessing.

13. The method according to claim 11, wherein the determining an amount of C-peptide bound to the incubated red blood cells comprises:
separating the incubated red blood cells from the incubated cellular mixture, forming an incubated red blood cell fraction and a supernatant; and
measuring
(i) the amount of C-peptide in the incubated red blood cell fraction; or
(ii) the amount of C-peptide in the supernatant; or
(iii) the amount of C-peptide in the supernatant, and subtracting the amount of C-peptide in the supernatant from a known amount of C-peptide; or
(iv) any combination of (i), (ii), and (iii).

14. The method according to claim 13, wherein the measuring comprises directly detecting C-peptide by detecting a signal provided by a tag coupled to the C-peptide or indirectly detecting C-peptide by detecting an antibody or antibody fraction that binds to the C-peptide.

15. The method according to claim 11, wherein the incubating comprises admixing (i) from about 0.05 mL to about 20 mL of a suspension of the red blood cells, (ii) about 1 to about 500 pmoles of the C-peptide, and (iii) the C-peptide binding facilitator to a final concentration of from about 0.05% (w/v) to about 25% (w/v).

* * * * *

SEQUENCE LISTING

<160> NUMBER OF SEQ ID NOS: 17

<210> SEQ ID NO 1
<211> LENGTH: 31
<212> TYPE: PRT
<213> ORGANISM: Homo sapiens

<400> SEQUENCE: 1

Glu Ala Glu Asp Leu Gln Val Gly Gln Val Glu Leu Gly Gly Gly Pro
1               5                   10                  15

Gly Ala Gly Ser Leu Gln Pro Leu Ala Leu Glu Gly Ser Leu Gln
            20                  25                  30

<210> SEQ ID NO 2
<211> LENGTH: 31
<212> TYPE: PRT
<213> ORGANISM: Sus scrofa

<400> SEQUENCE: 2

Glu Leu Glu Asp Pro Gln Val Glu Gln Thr Glu Leu Gly Met Gly Leu
1               5                   10                  15

Gly Ala Gly Gly Leu Gln Pro Leu Ala Leu Glu Met Ala Leu Gln
            20                  25                  30

<210> SEQ ID NO 3
<211> LENGTH: 26
<212> TYPE: PRT
<213> ORGANISM: Bos taurus

<400> SEQUENCE: 3

Glu Val Glu Gly Pro Gln Val Gly Ala Leu Glu Leu Ala Gly Gly Pro
1               5                   10                  15

Gly Ala Gly Gly Leu Glu Gly Pro Pro Gln
            20                  25

<210> SEQ ID NO 4
<211> LENGTH: 28
<212> TYPE: PRT
<213> ORGANISM: Gallus gallus

<400> SEQUENCE: 4

Asp Val Glu Gln Pro Leu Val Ser Ser Pro Leu Arg Gly Glu Ala Gly
1               5                   10                  15

Val Leu Pro Phe Gln Gln Glu Glu Tyr Glu Lys Val
            20                  25

<210> SEQ ID NO 5
<211> LENGTH: 31
<212> TYPE: PRT
<213> ORGANISM: Danio rerio

<400> SEQUENCE: 5

Asp Val Glu Pro Leu Leu Gly Phe Leu Pro Pro Lys Ser Ala Gln Glu
1               5                   10                  15

Thr Glu Val Ala Asp Phe Ala Phe Lys Asp His Ala Glu Leu Ile

```
            20                  25                  30
```

<210> SEQ ID NO 6
<211> LENGTH: 6
<212> TYPE: PRT
<213> ORGANISM: Artificial Sequence
<220> FEATURE:
<223> OTHER INFORMATION: 6-His tag

<400> SEQUENCE: 6

His His His His His His
1               5

<210> SEQ ID NO 7
<211> LENGTH: 9
<212> TYPE: PRT
<213> ORGANISM: Artificial Sequence
<220> FEATURE:
<223> OTHER INFORMATION: hemagglutinin tag

<400> SEQUENCE: 7

Tyr Pro Tyr Asp Val Pro Asp Tyr Ala
1               5

<210> SEQ ID NO 8
<211> LENGTH: 8
<212> TYPE: PRT
<213> ORGANISM: Artificial Sequence
<220> FEATURE:
<223> OTHER INFORMATION: FLAG tag

<400> SEQUENCE: 8

Asp Tyr Lys Asp Asp Asp Asp Lys
1               5

<210> SEQ ID NO 9
<211> LENGTH: 609
<212> TYPE: PRT
<213> ORGANISM: Homo sapiens

<400> SEQUENCE: 9

Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
                20                  25                  30

His Arg Phe Lys Asp Leu Gly Glu Glu Asn Phe Lys Ala Leu Val Leu
            35                  40                  45

Ile Ala Phe Ala Gln Tyr Leu Gln Gln Cys Pro Phe Glu Asp His Val
        50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
    130                 135                 140

Asp Val Met Cys Thr Ala Phe His Asp Asn Glu Glu Thr Phe Leu Lys
145                 150                 155                 160

-continued

```
Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
```

```
            580                 585                 590
Ala Glu Glu Gly Lys Lys Leu Val Ala Ala Ser Gln Ala Ala Leu Gly
            595                 600                 605

Leu

<210> SEQ ID NO 10
<211> LENGTH: 585
<212> TYPE: PRT
<213> ORGANISM: Homo sapiens

<400> SEQUENCE: 10

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
```

```
            340                 345                 350
Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375             380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 11
<211> LENGTH: 607
<212> TYPE: PRT
<213> ORGANISM: Bos taurus

<400> SEQUENCE: 11

Met Lys Trp Val Thr Phe Ile Ser Leu Leu Leu Leu Phe Ser Ser Ala
1               5                   10                  15

Tyr Ser Arg Gly Val Phe Arg Arg Asp Thr His Lys Ser Glu Ile Ala
            20                  25                  30

His Arg Phe Lys Asp Leu Gly Glu Glu His Phe Lys Gly Leu Val Leu
        35                  40                  45

Ile Ala Phe Ser Gln Tyr Leu Gln Gln Cys Pro Phe Asp Glu His Val
    50                  55                  60

Lys Leu Val Asn Glu Leu Thr Glu Phe Ala Lys Thr Cys Val Ala Asp
65                  70                  75                  80

Glu Ser His Ala Gly Cys Glu Lys Ser Leu His Thr Leu Phe Gly Asp
                85                  90                  95

Glu Leu Cys Lys Val Ala Ser Leu Arg Glu Thr Tyr Gly Asp Met Ala
            100                 105                 110

Asp Cys Cys Glu Lys Gln Glu Pro Glu Arg Asn Glu Cys Phe Leu Ser
        115                 120                 125
```

```
His Lys Asp Asp Ser Pro Asp Leu Pro Lys Leu Lys Pro Asp Pro Asn
    130                 135                 140

Thr Leu Cys Asp Glu Phe Lys Ala Asp Glu Lys Lys Phe Trp Gly Lys
145                 150                 155                 160

Tyr Leu Tyr Glu Ile Ala Arg Arg His Pro Tyr Phe Tyr Ala Pro Glu
                165                 170                 175

Leu Leu Tyr Tyr Ala Asn Lys Tyr Asn Gly Val Phe Gln Glu Cys Cys
                180                 185                 190

Gln Ala Glu Asp Lys Gly Ala Cys Leu Leu Pro Lys Ile Glu Thr Met
            195                 200                 205

Arg Glu Lys Val Leu Ala Ser Ser Ala Arg Gln Arg Leu Arg Cys Ala
    210                 215                 220

Ser Ile Gln Lys Phe Gly Glu Arg Ala Leu Lys Ala Trp Ser Val Ala
225                 230                 235                 240

Arg Leu Ser Gln Lys Phe Pro Lys Ala Glu Phe Val Glu Val Thr Lys
                245                 250                 255

Leu Val Thr Asp Leu Thr Lys Val His Lys Glu Cys Cys His Gly Asp
                260                 265                 270

Leu Leu Glu Cys Ala Asp Asp Arg Ala Asp Leu Ala Lys Tyr Ile Cys
            275                 280                 285

Asp Asn Gln Asp Thr Ile Ser Ser Lys Leu Lys Glu Cys Cys Asp Lys
    290                 295                 300

Pro Leu Leu Glu Lys Ser His Cys Ile Ala Glu Val Glu Lys Asp Ala
305                 310                 315                 320

Ile Pro Glu Asn Leu Pro Pro Leu Thr Ala Asp Phe Ala Glu Asp Lys
                325                 330                 335

Asp Val Cys Lys Asn Tyr Gln Glu Ala Lys Asp Ala Phe Leu Gly Ser
            340                 345                 350

Phe Leu Tyr Glu Tyr Ser Arg Arg His Pro Glu Tyr Ala Val Ser Val
    355                 360                 365

Leu Leu Arg Leu Ala Lys Glu Tyr Glu Ala Thr Leu Glu Glu Cys Cys
    370                 375                 380

Ala Lys Asp Asp Pro His Ala Cys Tyr Ser Thr Val Phe Asp Lys Leu
385                 390                 395                 400

Lys His Leu Val Asp Glu Pro Gln Asn Leu Ile Lys Gln Asn Cys Asp
                405                 410                 415

Gln Phe Glu Lys Leu Gly Glu Tyr Gly Phe Gln Asn Ala Leu Ile Val
            420                 425                 430

Arg Tyr Thr Arg Lys Val Pro Gln Val Ser Thr Pro Thr Leu Val Glu
    435                 440                 445

Val Ser Arg Ser Leu Gly Lys Val Gly Thr Arg Cys Cys Thr Lys Pro
450                 455                 460

Glu Ser Glu Arg Met Pro Cys Thr Glu Asp Tyr Leu Ser Leu Ile Leu
465                 470                 475                 480

Asn Arg Leu Cys Val Leu His Glu Lys Thr Pro Val Ser Glu Lys Val
                485                 490                 495

Thr Lys Cys Cys Thr Glu Ser Leu Val Asn Arg Arg Pro Cys Phe Ser
            500                 505                 510

Ala Leu Thr Pro Asp Glu Thr Tyr Val Pro Lys Ala Phe Asp Glu Lys
    515                 520                 525

Leu Phe Thr Phe His Ala Asp Ile Cys Thr Leu Pro Asp Thr Glu Lys
    530                 535                 540

Gln Ile Lys Lys Gln Thr Ala Leu Val Glu Leu Leu Lys His Lys Pro
```

```
                    545                 550                 555                 560
Lys Ala Thr Glu Glu Gln Leu Lys Thr Val Met Glu Asn Phe Val Ala
                565                 570                 575

Phe Val Asp Lys Cys Cys Ala Ala Asp Asp Lys Glu Ala Cys Phe Ala
                580                 585                 590

Val Glu Gly Pro Lys Leu Val Ser Thr Gln Thr Ala Leu Ala
                595                 600                 605

<210> SEQ ID NO 12
<211> LENGTH: 583
<212> TYPE: PRT
<213> ORGANISM: Bos taurus

<400> SEQUENCE: 12

Asp Thr His Lys Ser Glu Ile Ala His Arg Phe Lys Asp Leu Gly Glu
1               5                   10                  15

Glu His Phe Lys Gly Leu Val Leu Ile Ala Phe Ser Gln Tyr Leu Gln
                20                  25                  30

Gln Cys Pro Phe Asp Glu His Val Lys Leu Val Asn Glu Leu Thr Glu
            35                  40                  45

Phe Ala Lys Thr Cys Val Ala Asp Glu Ser His Ala Gly Cys Glu Lys
        50                  55                  60

Ser Leu His Thr Leu Phe Gly Asp Glu Leu Cys Lys Val Ala Ser Leu
65                  70                  75                  80

Arg Glu Thr Tyr Gly Asp Met Ala Asp Cys Cys Glu Lys Gln Glu Pro
                85                  90                  95

Glu Arg Asn Glu Cys Phe Leu Ser His Lys Asp Asp Ser Pro Asp Leu
                100                 105                 110

Pro Lys Leu Lys Pro Asp Pro Asn Thr Leu Cys Asp Glu Phe Lys Ala
            115                 120                 125

Asp Glu Lys Lys Phe Trp Gly Lys Tyr Leu Tyr Glu Ile Ala Arg Arg
        130                 135                 140

His Pro Tyr Phe Tyr Ala Pro Glu Leu Leu Tyr Tyr Ala Asn Lys Tyr
145                 150                 155                 160

Asn Gly Val Phe Gln Glu Cys Cys Gln Ala Glu Asp Lys Gly Ala Cys
                165                 170                 175

Leu Leu Pro Lys Ile Glu Thr Met Arg Glu Lys Val Leu Ala Ser Ser
            180                 185                 190

Ala Arg Gln Arg Leu Arg Cys Ala Ser Ile Gln Lys Phe Gly Glu Arg
        195                 200                 205

Ala Leu Lys Ala Trp Ser Val Ala Arg Leu Ser Gln Lys Phe Pro Lys
        210                 215                 220

Ala Glu Phe Val Glu Val Thr Lys Leu Val Thr Asp Leu Thr Lys Val
225                 230                 235                 240

His Lys Glu Cys Cys His Gly Asp Leu Leu Glu Cys Ala Asp Asp Arg
                245                 250                 255

Ala Asp Leu Ala Lys Tyr Ile Cys Asp Asn Gln Asp Thr Ile Ser Ser
            260                 265                 270

Lys Leu Lys Glu Cys Cys Asp Lys Pro Leu Leu Glu Lys Ser His Cys
        275                 280                 285

Ile Ala Glu Val Glu Lys Asp Ala Ile Pro Glu Asn Leu Pro Pro Leu
        290                 295                 300

Thr Ala Asp Phe Ala Glu Asp Lys Asp Val Cys Lys Asn Tyr Gln Glu
305                 310                 315                 320
```

```
Ala Lys Asp Ala Phe Leu Gly Ser Phe Leu Tyr Glu Tyr Ser Arg Arg
            325                 330                 335

His Pro Glu Tyr Ala Val Ser Val Leu Leu Arg Leu Ala Lys Glu Tyr
        340                 345                 350

Glu Ala Thr Leu Glu Glu Cys Cys Ala Lys Asp Asp Pro His Ala Cys
            355                 360                 365

Tyr Ser Thr Val Phe Asp Lys Leu Lys His Leu Val Asp Glu Pro Gln
        370                 375                 380

Asn Leu Ile Lys Gln Asn Cys Asp Gln Phe Glu Lys Leu Gly Glu Tyr
385                 390                 395                 400

Gly Phe Gln Asn Ala Leu Ile Val Arg Tyr Thr Arg Lys Val Pro Gln
                405                 410                 415

Val Ser Thr Pro Thr Leu Val Glu Val Ser Arg Ser Leu Gly Lys Val
            420                 425                 430

Gly Thr Arg Cys Cys Thr Lys Pro Glu Ser Glu Arg Met Pro Cys Thr
        435                 440                 445

Glu Asp Tyr Leu Ser Leu Ile Leu Asn Arg Leu Cys Val Leu His Glu
    450                 455                 460

Lys Thr Pro Val Ser Glu Lys Val Thr Lys Cys Cys Thr Glu Ser Leu
465                 470                 475                 480

Val Asn Arg Arg Pro Cys Phe Ser Ala Leu Thr Pro Asp Glu Thr Tyr
                485                 490                 495

Val Pro Lys Ala Phe Asp Glu Lys Leu Phe Thr Phe His Ala Asp Ile
            500                 505                 510

Cys Thr Leu Pro Asp Thr Glu Lys Gln Ile Lys Lys Gln Thr Ala Leu
        515                 520                 525

Val Glu Leu Leu Lys His Lys Pro Lys Ala Thr Glu Glu Gln Leu Lys
    530                 535                 540

Thr Val Met Glu Asn Phe Val Ala Phe Val Asp Lys Cys Cys Ala Ala
545                 550                 555                 560

Asp Asp Lys Glu Ala Cys Phe Ala Val Glu Gly Pro Lys Leu Val Val
                565                 570                 575

Ser Thr Gln Thr Ala Leu Ala
            580

<210> SEQ ID NO 13
<211> LENGTH: 615
<212> TYPE: PRT
<213> ORGANISM: Gallus gallus

<400> SEQUENCE: 13

Met Lys Trp Val Thr Leu Ile Ser Phe Ile Phe Leu Phe Ser Ser Ala
1               5                   10                  15

Thr Ser Arg Asn Leu Gln Arg Phe Ala Arg Asp Ala Glu His Lys Ser
            20                  25                  30

Glu Ile Ala His Arg Tyr Asn Asp Leu Lys Glu Glu Thr Phe Lys Ala
        35                  40                  45

Val Ala Met Ile Thr Phe Ala Gln Tyr Leu Gln Arg Cys Ser Tyr Glu
    50                  55                  60

Gly Leu Ser Lys Leu Val Lys Asp Val Val Asp Leu Ala Gln Lys Cys
65                  70                  75                  80

Val Ala Asn Glu Asp Ala Pro Glu Cys Ser Lys Pro Leu Pro Ser Ile
                85                  90                  95

Ile Leu Asp Glu Ile Cys Gln Val Glu Lys Leu Arg Asp Ser Tyr Gly
            100                 105                 110
```

```
Ala Met Ala Asp Cys Cys Ser Lys Ala Asp Pro Glu Arg Asn Glu Cys
        115                 120                 125
Phe Leu Ser Phe Lys Val Ser Gln Pro Asp Phe Val Gln Pro Tyr Gln
130                 135                 140
Arg Pro Ala Ser Asp Val Ile Cys Gln Glu Tyr Gln Asp Asn Arg Val
145                 150                 155                 160
Ser Phe Leu Gly His Phe Ile Tyr Ser Val Ala Arg Arg His Pro Phe
                165                 170                 175
Leu Tyr Ala Pro Ala Ile Leu Ser Phe Ala Val Asp Phe Glu His Ala
            180                 185                 190
Leu Gln Ser Cys Cys Lys Glu Ser Asp Val Gly Ala Cys Leu Asp Thr
        195                 200                 205
Lys Glu Ile Val Met Arg Glu Lys Ala Lys Gly Val Ser Val Lys Gln
210                 215                 220
Gln Tyr Phe Cys Gly Ile Leu Lys Gln Phe Gly Asp Arg Val Phe Gln
225                 230                 235                 240
Ala Arg Gln Leu Ile Tyr Leu Ser Gln Lys Tyr Pro Lys Ala Pro Phe
                245                 250                 255
Ser Glu Val Ser Lys Phe Val His Asp Ser Ile Gly Val His Lys Glu
            260                 265                 270
Cys Cys Glu Gly Asp Met Val Glu Cys Met Asp Asp Met Ala Arg Met
        275                 280                 285
Met Ser Asn Leu Cys Ser Gln Gln Asp Val Phe Ser Gly Lys Ile Lys
290                 295                 300
Asp Cys Cys Glu Lys Pro Ile Val Glu Arg Ser Gln Cys Ile Met Glu
305                 310                 315                 320
Ala Glu Phe Asp Glu Lys Pro Ala Asp Leu Pro Ser Leu Val Glu Lys
                325                 330                 335
Tyr Ile Glu Asp Lys Glu Val Cys Lys Ser Phe Glu Ala Gly His Asp
            340                 345                 350
Ala Phe Met Ala Glu Phe Val Tyr Glu Tyr Ser Arg Arg His Pro Glu
        355                 360                 365
Phe Ser Ile Gln Leu Ile Met Arg Ile Ala Lys Gly Tyr Glu Ser Leu
370                 375                 380
Leu Glu Lys Cys Cys Lys Thr Asp Asn Pro Ala Glu Cys Tyr Ala Asn
385                 390                 395                 400
Ala Gln Glu Gln Leu Asn Gln His Ile Lys Glu Thr Gln Asp Val Val
                405                 410                 415
Lys Thr Asn Cys Asp Leu Leu His Asp His Gly Glu Ala Asp Phe Leu
            420                 425                 430
Lys Ser Ile Leu Ile Arg Tyr Thr Lys Lys Met Pro Gln Val Pro Thr
        435                 440                 445
Asp Leu Leu Leu Glu Thr Gly Lys Lys Met Thr Thr Ile Gly Thr Lys
450                 455                 460
Cys Cys Gln Leu Gly Glu Asp Arg Arg Met Ala Cys Ser Glu Gly Tyr
465                 470                 475                 480
Leu Ser Ile Val Ile His Asp Thr Cys Arg Lys Gln Glu Thr Thr Pro
                485                 490                 495
Ile Asn Asp Asn Val Ser Gln Cys Cys Ser Gln Leu Tyr Ala Asn Arg
            500                 505                 510
Arg Pro Cys Phe Thr Ala Met Gly Val Asp Thr Lys Tyr Val Pro Pro
        515                 520                 525
```

```
Pro Phe Asn Pro Asp Met Phe Ser Phe Asp Glu Lys Leu Cys Ser Ala
    530                 535                 540

Pro Ala Glu Glu Arg Glu Val Gly Gln Met Lys Leu Leu Ile Asn Leu
545                 550                 555                 560

Ile Lys Arg Lys Pro Gln Met Thr Glu Glu Gln Ile Lys Thr Ile Ala
                565                 570                 575

Asp Gly Phe Thr Ala Met Val Asp Lys Cys Cys Lys Gln Ser Asp Ile
            580                 585                 590

Asn Thr Cys Phe Gly Glu Glu Gly Ala Asn Leu Ile Val Gln Ser Arg
        595                 600                 605

Ala Thr Leu Gly Ile Gly Ala
    610                 615

<210> SEQ ID NO 14
<211> LENGTH: 592
<212> TYPE: PRT
<213> ORGANISM: Gallus gallus

<400> SEQUENCE: 14

Phe Ala Arg Asp Ala Glu His Lys Ser Glu Ile Ala His Arg Tyr Asn
1               5                   10                  15

Asp Leu Lys Glu Glu Thr Phe Lys Ala Val Ala Met Ile Thr Phe Ala
            20                  25                  30

Gln Tyr Leu Gln Arg Cys Ser Tyr Glu Gly Leu Ser Lys Leu Val Lys
        35                  40                  45

Asp Val Val Asp Leu Ala Gln Lys Cys Val Ala Asn Glu Asp Ala Pro
    50                  55                  60

Glu Cys Ser Lys Pro Leu Pro Ser Ile Ile Leu Asp Glu Ile Cys Gln
65                  70                  75                  80

Val Glu Lys Leu Arg Asp Ser Tyr Gly Ala Met Ala Asp Cys Cys Ser
                85                  90                  95

Lys Ala Asp Pro Glu Arg Asn Glu Cys Phe Leu Ser Phe Lys Val Ser
            100                 105                 110

Gln Pro Asp Phe Val Gln Pro Tyr Gln Arg Pro Ala Ser Asp Val Ile
        115                 120                 125

Cys Gln Glu Tyr Gln Asp Asn Arg Val Ser Phe Leu Gly His Phe Ile
    130                 135                 140

Tyr Ser Val Ala Arg Arg His Pro Phe Leu Tyr Ala Pro Ala Ile Leu
145                 150                 155                 160

Ser Phe Ala Val Asp Phe Glu His Ala Leu Gln Ser Cys Cys Lys Glu
                165                 170                 175

Ser Asp Val Gly Ala Cys Leu Asp Thr Lys Glu Ile Val Met Arg Glu
            180                 185                 190

Lys Ala Lys Gly Val Ser Val Lys Gln Gln Tyr Phe Cys Gly Ile Leu
        195                 200                 205

Lys Gln Phe Gly Asp Arg Val Phe Gln Ala Arg Gln Leu Ile Tyr Leu
    210                 215                 220

Ser Gln Lys Tyr Pro Lys Ala Pro Phe Ser Glu Val Ser Lys Phe Val
225                 230                 235                 240

His Asp Ser Ile Gly Val His Lys Glu Cys Cys Glu Gly Asp Met Val
                245                 250                 255

Glu Cys Met Asp Asp Met Ala Arg Met Met Ser Asn Leu Cys Ser Gln
            260                 265                 270

Gln Asp Val Phe Ser Gly Lys Ile Lys Asp Cys Cys Glu Lys Pro Ile
        275                 280                 285
```

Val Glu Arg Ser Gln Cys Ile Met Glu Ala Glu Phe Asp Glu Lys Pro
    290                 295                 300

Ala Asp Leu Pro Ser Leu Val Glu Lys Tyr Ile Glu Asp Lys Glu Val
305                 310                 315                 320

Cys Lys Ser Phe Glu Ala Gly His Asp Ala Phe Met Ala Glu Phe Val
                325                 330                 335

Tyr Glu Tyr Ser Arg Arg His Pro Glu Phe Ser Ile Gln Leu Ile Met
                340                 345                 350

Arg Ile Ala Lys Gly Tyr Glu Ser Leu Leu Glu Lys Cys Cys Lys Thr
                355                 360                 365

Asp Asn Pro Ala Glu Cys Tyr Ala Asn Ala Gln Glu Gln Leu Asn Gln
            370                 375                 380

His Ile Lys Glu Thr Gln Asp Val Val Lys Thr Asn Cys Asp Leu Leu
385                 390                 395                 400

His Asp His Gly Glu Ala Asp Phe Leu Lys Ser Ile Leu Ile Arg Tyr
                405                 410                 415

Thr Lys Lys Met Pro Gln Val Pro Thr Asp Leu Leu Leu Glu Thr Gly
                420                 425                 430

Lys Lys Met Thr Thr Ile Gly Thr Lys Cys Cys Gln Leu Gly Glu Asp
            435                 440                 445

Arg Arg Met Ala Cys Ser Glu Gly Tyr Leu Ser Ile Val Ile His Asp
450                 455                 460

Thr Cys Arg Lys Gln Glu Thr Thr Pro Ile Asn Asp Asn Val Ser Gln
465                 470                 475                 480

Cys Cys Ser Gln Leu Tyr Ala Asn Arg Arg Pro Cys Phe Thr Ala Met
                485                 490                 495

Gly Val Asp Thr Lys Tyr Val Pro Pro Pro Phe Asn Pro Asp Met Phe
                500                 505                 510

Ser Phe Asp Glu Lys Leu Cys Ser Ala Pro Ala Glu Glu Arg Glu Val
                515                 520                 525

Gly Gln Met Lys Leu Leu Ile Asn Leu Ile Lys Arg Lys Pro Gln Met
            530                 535                 540

Thr Glu Glu Gln Ile Lys Thr Ile Ala Asp Gly Phe Thr Ala Met Val
545                 550                 555                 560

Asp Lys Cys Cys Lys Gln Ser Asp Ile Asn Thr Cys Phe Gly Glu Glu
                565                 570                 575

Gly Ala Asn Leu Ile Val Gln Ser Arg Ala Thr Leu Gly Ile Gly Ala
                580                 585                 590

<210> SEQ ID NO 15
<211> LENGTH: 607
<212> TYPE: PRT
<213> ORGANISM: Sus scrofa

<400> SEQUENCE: 15

Met Lys Trp Val Thr Phe Ile Ser Leu Leu Phe Leu Phe Ser Ser Ala
1               5                   10                  15

Tyr Ser Arg Gly Val Phe Arg Arg Asp Thr Tyr Lys Ser Glu Ile Ala
            20                  25                  30

His Arg Phe Lys Asp Leu Gly Glu Gln Tyr Phe Lys Gly Leu Val Leu
        35                  40                  45

Ile Ala Phe Ser Gln His Leu Gln Gln Cys Pro Tyr Glu Glu His Val
    50                  55                  60

Lys Leu Val Arg Glu Val Thr Glu Phe Ala Lys Thr Cys Val Ala Asp

```
            65                  70                  75                  80
Glu Ser Ala Glu Asn Cys Asp Lys Ser Ile His Thr Leu Phe Gly Asp
                    85                  90                  95
Lys Leu Cys Ala Ile Pro Ser Leu Arg Glu His Tyr Gly Asp Leu Ala
                100                 105                 110
Asp Cys Cys Glu Lys Glu Glu Pro Glu Arg Asn Glu Cys Phe Leu Gln
                115                 120                 125
His Lys Asn Asp Asn Pro Asp Ile Pro Lys Leu Lys Pro Asp Pro Val
            130                 135                 140
Ala Leu Cys Ala Asp Phe Gln Glu Asp Glu Gln Lys Phe Trp Gly Lys
145                 150                 155                 160
Tyr Leu Tyr Glu Ile Ala Arg Arg His Pro Tyr Phe Tyr Ala Pro Glu
                165                 170                 175
Leu Leu Tyr Tyr Ala Ile Ile Tyr Lys Asp Val Phe Ser Glu Cys Cys
                180                 185                 190
Gln Ala Ala Asp Lys Ala Ala Cys Leu Leu Pro Lys Ile Glu His Leu
            195                 200                 205
Arg Glu Lys Val Leu Thr Ser Ala Ala Lys Gln Arg Leu Lys Cys Ala
210                 215                 220
Ser Ile Gln Lys Phe Gly Glu Arg Ala Phe Lys Ala Trp Ser Leu Ala
225                 230                 235                 240
Arg Leu Ser Gln Arg Phe Pro Lys Ala Asp Phe Thr Glu Ile Ser Lys
                245                 250                 255
Ile Val Thr Asp Leu Ala Lys Val His Lys Glu Cys Cys His Gly Asp
                260                 265                 270
Leu Leu Glu Cys Ala Asp Asp Arg Ala Asp Leu Ala Lys Tyr Ile Cys
            275                 280                 285
Glu Asn Gln Asp Thr Ile Ser Thr Lys Leu Lys Glu Cys Cys Asp Lys
            290                 295                 300
Pro Leu Leu Glu Lys Ser His Cys Ile Ala Glu Ala Lys Arg Asp Glu
305                 310                 315                 320
Leu Pro Ala Asp Leu Asn Pro Leu Glu His Asp Phe Val Glu Asp Lys
                325                 330                 335
Glu Val Cys Lys Asn Tyr Lys Glu Ala Lys His Val Phe Leu Gly Thr
                340                 345                 350
Phe Leu Tyr Glu Tyr Ser Arg Arg His Pro Asp Tyr Ser Val Ser Leu
            355                 360                 365
Leu Leu Arg Ile Ala Lys Ile Tyr Glu Ala Thr Leu Glu Asp Cys Cys
            370                 375                 380
Ala Lys Glu Asp Pro Pro Ala Cys Tyr Ala Thr Val Phe Asp Lys Phe
385                 390                 395                 400
Gln Pro Leu Val Asp Glu Pro Lys Asn Leu Ile Lys Gln Asn Cys Glu
                405                 410                 415
Leu Phe Glu Lys Leu Gly Glu Tyr Gly Phe Gln Asn Ala Leu Ile Val
            420                 425                 430
Arg Tyr Thr Lys Lys Val Pro Gln Val Ser Thr Pro Thr Leu Val Glu
            435                 440                 445
Val Ala Arg Lys Leu Gly Leu Val Gly Ser Arg Cys Cys Lys Arg Pro
450                 455                 460
Glu Glu Glu Arg Leu Ser Cys Ala Glu Asp Tyr Leu Ser Leu Val Leu
465                 470                 475                 480
Asn Arg Leu Cys Val Leu His Glu Lys Thr Pro Val Ser Glu Lys Val
                485                 490                 495
```

```
Thr Lys Cys Cys Thr Glu Ser Leu Val Asn Arg Arg Pro Cys Phe Ser
            500                 505                 510

Ala Leu Thr Pro Asp Glu Thr Tyr Lys Pro Lys Glu Phe Val Glu Gly
            515                 520                 525

Thr Phe Thr Phe His Ala Asp Leu Cys Thr Leu Pro Glu Asp Glu Lys
            530                 535                 540

Gln Ile Lys Lys Gln Thr Ala Leu Val Glu Leu Leu Lys His Lys Pro
545                 550                 555                 560

His Ala Thr Glu Glu Gln Leu Arg Thr Val Leu Gly Asn Phe Ala Ala
                565                 570                 575

Phe Val Gln Lys Cys Cys Ala Ala Pro Asp His Glu Ala Cys Phe Ala
            580                 585                 590

Val Glu Gly Pro Lys Phe Val Ile Glu Ile Arg Gly Ile Leu Ala
            595                 600                 605

<210> SEQ ID NO 16
<211> LENGTH: 583
<212> TYPE: PRT
<213> ORGANISM: Sus scrofa

<400> SEQUENCE: 16

Asp Thr Tyr Lys Ser Glu Ile Ala His Arg Phe Lys Asp Leu Gly Glu
1               5                   10                  15

Gln Tyr Phe Lys Gly Leu Val Leu Ile Ala Phe Ser Gln His Leu Gln
            20                  25                  30

Gln Cys Pro Tyr Glu Glu His Val Lys Leu Val Arg Glu Val Thr Glu
        35                  40                  45

Phe Ala Lys Thr Cys Val Ala Asp Glu Ser Ala Glu Asn Cys Asp Lys
    50                  55                  60

Ser Ile His Thr Leu Phe Gly Asp Lys Leu Cys Ala Ile Pro Ser Leu
65                  70                  75                  80

Arg Glu His Tyr Gly Asp Leu Ala Asp Cys Cys Glu Lys Glu Glu Pro
                85                  90                  95

Glu Arg Asn Glu Cys Phe Leu Gln His Lys Asn Asp Asn Pro Asp Ile
            100                 105                 110

Pro Lys Leu Lys Pro Asp Pro Val Ala Leu Cys Ala Asp Phe Gln Glu
        115                 120                 125

Asp Glu Gln Lys Phe Trp Gly Lys Tyr Leu Tyr Glu Ile Ala Arg Arg
    130                 135                 140

His Pro Tyr Phe Tyr Ala Pro Glu Leu Leu Tyr Tyr Ala Ile Ile Tyr
145                 150                 155                 160

Lys Asp Val Phe Ser Glu Cys Cys Gln Ala Ala Asp Lys Ala Ala Cys
                165                 170                 175

Leu Leu Pro Lys Ile Glu His Leu Arg Glu Lys Val Leu Thr Ser Ala
            180                 185                 190

Ala Lys Gln Arg Leu Lys Cys Ala Ser Ile Gln Lys Phe Gly Glu Arg
        195                 200                 205

Ala Phe Lys Ala Trp Ser Leu Ala Arg Leu Ser Gln Arg Phe Pro Lys
    210                 215                 220

Ala Asp Phe Thr Glu Ile Ser Lys Ile Val Thr Asp Leu Ala Lys Val
225                 230                 235                 240

His Lys Glu Cys Cys His Gly Asp Leu Leu Glu Cys Ala Asp Asp Arg
                245                 250                 255

Ala Asp Leu Ala Lys Tyr Ile Cys Glu Asn Gln Asp Thr Ile Ser Thr
```

```
                    260                 265                 270
Lys Leu Lys Glu Cys Cys Asp Lys Pro Leu Glu Lys Ser His Cys
            275                 280                 285
Ile Ala Glu Ala Lys Arg Asp Glu Leu Pro Ala Asp Leu Asn Pro Leu
290                 295                 300
Glu His Asp Phe Val Asp Lys Glu Val Cys Lys Asn Tyr Lys Glu
305                 310                 315                 320
Ala Lys His Val Phe Leu Gly Thr Phe Leu Tyr Glu Tyr Ser Arg Arg
                325                 330                 335
His Pro Asp Tyr Ser Val Ser Leu Leu Leu Arg Ile Ala Lys Ile Tyr
            340                 345                 350
Glu Ala Thr Leu Glu Asp Cys Cys Ala Lys Glu Asp Pro Pro Ala Cys
                355                 360                 365
Tyr Ala Thr Val Phe Asp Lys Phe Gln Pro Leu Val Asp Glu Pro Lys
            370                 375                 380
Asn Leu Ile Lys Gln Asn Cys Glu Leu Phe Glu Lys Leu Gly Glu Tyr
385                 390                 395                 400
Gly Phe Gln Asn Ala Leu Ile Val Arg Tyr Thr Lys Lys Val Pro Gln
                405                 410                 415
Val Ser Thr Pro Thr Leu Val Glu Val Ala Arg Lys Leu Gly Leu Val
            420                 425                 430
Gly Ser Arg Cys Cys Lys Arg Pro Glu Glu Glu Arg Leu Ser Cys Ala
            435                 440                 445
Glu Asp Tyr Leu Ser Leu Val Leu Asn Arg Leu Cys Val Leu His Glu
            450                 455                 460
Lys Thr Pro Val Ser Glu Lys Val Thr Lys Cys Cys Thr Glu Ser Leu
465                 470                 475                 480
Val Asn Arg Arg Pro Cys Phe Ser Ala Leu Thr Pro Asp Glu Thr Tyr
                485                 490                 495
Lys Pro Lys Glu Phe Val Glu Gly Thr Phe Thr Phe His Ala Asp Leu
                500                 505                 510
Cys Thr Leu Pro Glu Asp Glu Lys Gln Ile Lys Lys Gln Thr Ala Leu
            515                 520                 525
Val Glu Leu Leu Lys His Lys Pro His Ala Thr Glu Glu Gln Leu Arg
            530                 535                 540
Thr Val Leu Gly Asn Phe Ala Ala Phe Val Gln Lys Cys Cys Ala Ala
545                 550                 555                 560
Pro Asp His Glu Ala Cys Phe Ala Val Glu Gly Pro Lys Phe Val Ile
                565                 570                 575
Glu Ile Arg Gly Ile Leu Ala
            580

<210> SEQ ID NO 17
<211> LENGTH: 5
<212> TYPE: PRT
<213> ORGANISM: Artificial Sequence
<220> FEATURE:
<223> OTHER INFORMATION: synthetic peptide

<400> SEQUENCE: 17

Glu Gly Ser Leu Gln
1               5
```